(12) United States Patent
Terrett

(10) Patent No.: US 7,297,760 B2
(45) Date of Patent: Nov. 20, 2007

(54) CANCER ASSOCIATED PROTEIN

(75) Inventor: Jonathan Alexander Terrett, Abingdon (GB)

(73) Assignee: UCB Pharma S.A., Brussels (BE)

( * ) Notice: Subject to any disclaimer, the term of this patent is extended or adjusted under 35 U.S.C. 154(b) by 595 days.

(21) Appl. No.: 10/736,227

(22) Filed: Dec. 15, 2003

(65) Prior Publication Data

US 2004/0142367 A1 Jul. 22, 2004

Related U.S. Application Data

(63) Continuation of application No. PCT/GB02/02782, filed on Jun. 14, 2002.

(30) Foreign Application Priority Data

Jun. 15, 2001 (GB) ................................. 0114643.0
Mar. 6, 2002 (GB) ................................. 0205264.5

(51) Int. Cl.
*A61K 38/00* (2006.01)
*C07K 14/00* (2006.01)
*C07K 16/00* (2006.01)
*C07K 17/00* (2006.01)
*C07K 2/00* (2006.01)
*C07K 4/00* (2006.01)
*C07K 5/00* (2006.01)
*C12N 15/00* (2006.01)
*C12N 15/09* (2006.01)
*C12N 15/63* (2006.01)
*C12N 15/70* (2006.01)
*C12N 15/74* (2006.01)

(52) U.S. Cl. ...................... 530/300; 530/350; 530/326; 530/328; 436/64; 436/86

(58) Field of Classification Search ................ 530/300, 530/350, 326, 328; 436/64, 86
See application file for complete search history.

(56) References Cited

U.S. PATENT DOCUMENTS 5,776,687 A * 7/1998 Nagpal et al. .................. 435/6
2003/0092898 A1* 5/2003 Salceda et al. ............. 536/23.1

FOREIGN PATENT DOCUMENTS

| WO | WO 00/55628 | 9/2000 |
| WO | WO 01/13117 A2 | 2/2001 |
| WO | WO 01/13117 A3 | 2/2001 |
| WO | WO 02/64611 | 8/2002 |

OTHER PUBLICATIONS

Amino acid databases, GenCore. Sequence alignment between US 2003/0092898 A1 sequence 267 and Applicants' SEQ ID No: 1, May 15, 2003.*

Amino acid databases, GenCore. Sequence alignment between US Patent 5,776,687 sequence 12 and Applicants' SEQ ID No: 1, Jul. 7, 1998.*

Baselga, J., et al., Recombinant Humanized Anti-HER2 Antibody(Herceptin™)Enhances the Antitumor Activity of Paclitaxel and Doxorubicin against HER2/neu Overexpressing Human Breast Cancer Xenografts[1], 1998, Cancer Res. 58: 2825-2831.

Catimel, B., et al., Purification and Characterization of a Novel Restricted Antigen Expressed by Normal and Transformed Human Colonic Epithelium, 1996, J. Biol. Chem. 271:25664-25670.

ABSTRACT for Craggs, et al., 2003, Applied Genomics & Proteomics 2(2):101-100.

Davis, ID,et al.,An overview of Cancer immunotherapy,2000, Immunol Cell Biol. 78: 179-196.

Dillman, R.O.,Perceptions of Herceptin®:A Monoclonal Antibody for the Treatment of Breast Cancer, 1999, Cancer Biother. Radiopham. 14: 5-10.

Green,MC,etal,Monoclonal antibody therapy for solid tumors,2000,Cancer Treat Rev 26:269-86.

Hubert, R.S. et al., STEAP: A prostate-specific cell-surface antigen highly expressed in human prostate tumors, 1999, Pro. Natl Acad. Sci. USA 96: 14523-14528.

Knuth, A. et al., Cancer immunotherapy in clinical oncology,2000, Cancer Chemother. Pharmacol. 46, S46-51.

Lucas S., et al., MAGE-5B, MAGE-B6, MAGE-C2, and MAGE-C3: Four New Members Of The MAGE Family With Tumor-Specific Expression, 2000, Int.J. Cancer 87:55-60.

Miller, K.D., et al., Toward checkmate:biology and breast cancer therapy for the new millennium, 1999, Invest.New Drugs 17: 417-427.

Saffran, D.C., et al., Targget antigens for prostate cancer immunotherapy, 1999, Cancer Metastasis Rev. 18: 437-449.

Shiku, H., et al.,Development of a cancer vaccine: peptides, proteins, and DNA 2000, Cancer Chemother. Pharmacol. 46:S77-82.

Stebbing, J., et al.,Herceptin (transtuzamab) in advanced breast cancer, 2000, Cancer Treat. Rev. 26:287-290.

Vermeulen, S.J., et al., The αE-catenin gene (CTNNA1) acts as an invasion-suppressor gene in human colon cancer cells, 1999, Oncogene 18: 905-915.

Database EMBL online Dec. 1, 2001 "NSE2 Protein" Database Accession No. Q96Kn1 XP002234948.

* cited by examiner

*Primary Examiner*—Alana M. Harris
(74) *Attorney, Agent, or Firm*—Klauber & Jackson

(57) ABSTRACT

The present invention relates to a novel polypeptide (BCMP 101) compositions comprising the polypeptide, including vaccines, and antibodies that are immunospecific for the polypeptide. The use of the polypeptide in the diagnosis, prophylaxis and treatment of cancer, in particular breast cancer is also provided.

3 Claims, 7 Drawing Sheets

Figure 1

Figure 2:
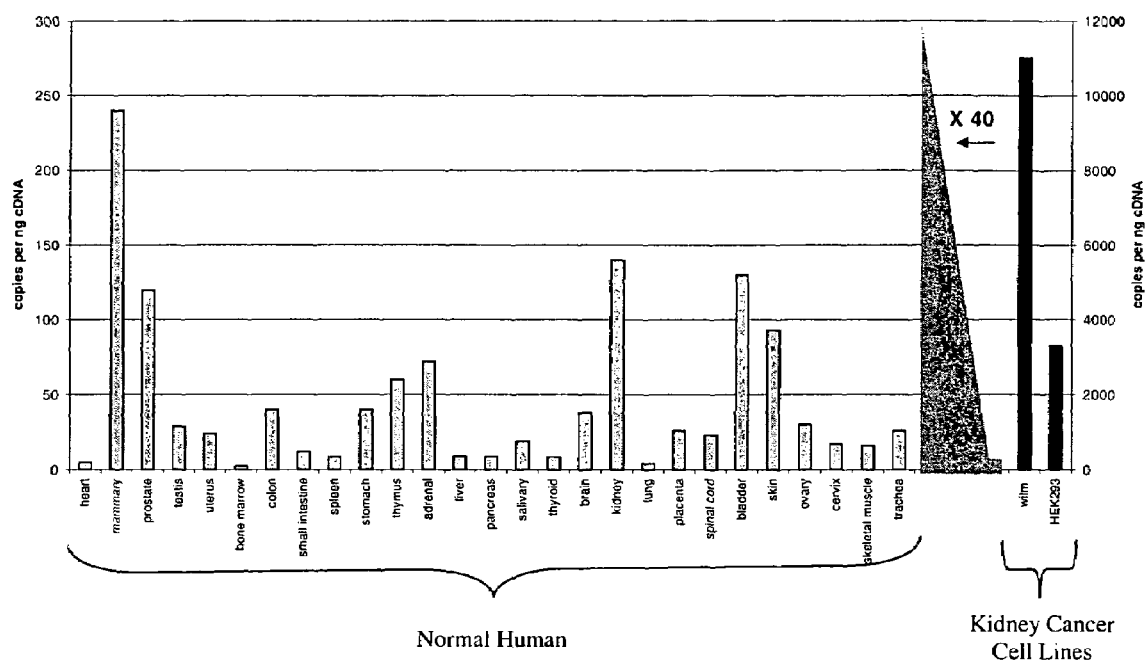

| | |
|---|---|
| TGTGCAAATGACCCTGGAGTTGGTTTCGCTTTCTCCCCTTGCGGCGGTGTGAACGTGTGT | 60 |
| CCGCAGCGTATGGGCAACCAGGTGGAGAAATTGACCCACCTAAGTTACAAGGAAGTTCC | 120 |
|          M  G  N  Q  V  E  K  <u>L  T  H  L  S  Y  K  E  V  P</u> | 17 |
| CACGGCCGACCCGACTGGCGTGGACCGGGACGACGGGCCCCGCATTGGGGTCTCCTACAT | 180 |
| <u>T  A  D  P  T  G  V  D  R</u>  D  D  G  P  R  I  G  V  S  Y  I | 37 |
| TTTCTCCAATGACGATGAGGACGTGGAGCCGCAGCCGCCGCCTCAGGGGCCAGATGGCGG | 240 |
|  F  S  N  D  D  E  D  V  E  P  Q  P  P  P  Q  G  P  D  G  G | 57 |
| CGGCTTGCCCGACGGTGGGGACGGGCCGCCGCCGCCCAGCCGCAGCCCTACGATCCGCG | 300 |
|  G  L  P  D  G  G  D  G  P  P  P  P  Q  P  Q  P  Y  D  P  R | 77 |
| GCTGCACGAGGTGGAATGCTCCGTGTTCTACCGGGACGAATGCATCTACCAGAAGAGCTT | 360 |
|  L  H  E  V  E  C  S  V  F  Y  R  D  E  C  I  Y  Q  K  S  F | 97 |
| CGCGCCGGGCTCGGCGGCGCTGAGTACCTACACGCCCGAGAACCTGCTCAACAAGTGCAA | 420 |
|  A  P  G  S  A  A  L  S  T  Y  T  P  E  N  L  L  N  K  C  K | 117 |
| GCCGGGCGATCTGGTGGAGTTCGTGTCGCAGGCTCAGTACCCGCACTGGGCCGTATATGT | 480 |
|  P  G  D  L  V  E  F  V  S  Q  A  Q  Y  P  H  W  A  V  Y  V | 137 |
| GGGTAACTTCCAGGTGGTGCACCTGCACCGGCTGGAGGTGATTAACAGCTTCCTGACTGA | 540 |
|  G  N  F  Q  V  V  H  L  H  R  <u>L  E  V  I  N  S  F  L  T  D</u> | 157 |
| CGCCAGCCAGGGCCGTCGCGGCCGCGTGGTCAACGATCTGTACCGCTACAAGCCGCTAAG | 600 |
|  <u>A  S  Q  G  R</u>  R  G  R  V  V  N  D  L  Y  R  Y  K  P  L  S | 177 |
| CTCCAGCGCCGTGGTGCGCAACGCGCTGGCGCACGTGGGTGCCAAGGAGCGCGAGCTGAG | 660 |
|  S  S  A  V  V  R  N  A  L  A  H  V  G  A  K  E  R  E  L  S | 197 |
| CTGGCGCAACTCGGAGAGTTTCGCCGCCTGGTGCCGCTACGGCAAGCGCGAGTTCAAGAT | 720 |
|  W  R  *__N__  __S__  __E__  __S__  __F__  __A__  __A__  __W__  __C__  __R__*  Y  G  K  R  E  F  K  I | 217 |
| CGGCGGCGAGCTGCGCATCGGCAAGCAGCCCTACCGGCTGCAGATTCAGCTGTCGGCGCA | 780 |
|  G  G  E  L  R  I  G  K  Q  P  Y  R  L  Q  I  Q  L  S  A  Q | 237 |
| GCGCAGCCACACGCTCGAGTTCCAGAGTCTAGAGGACCTGATCATGGAGAAGCGACGCAA | 840 |
|  R  S  H  T  L  E  F  Q  S  L  E  D  L  I  M  E  K  R  R  N | 257 |
| CGACCAGATCGGGCGCGCGGCCGTGCTGCAGGAGCTCGCCACGCACCTGCACCCGGCGGA | 900 |
|  D  Q  I  G  R  A  A  V  L  Q  E  L  A  T  H  L  H  P  A  E | 277 |
| GCCGGAGGAGGGCGACAGCAACGTGGCGCGGACTACGCCGCCTCCCGGGCGCCCCCTGC | 960 |
|  P  E  E  G  D  S  N  V  A  R  T  T  P  P  G  R  P  P  A | 297 |
| GCCCAGCTCCGAGGAGGAGGACGGAGAGGCAGTGGCACACTGATGGGCGAGCTGAGCGCA | 1020 |
|  P  S  S  E  E  E  D  G  E  A  V  A  H  * | 310 |
| GAGCTGCGAAGGGGAACTGTTTGCAGTAGCAGCC | 1054 |

CANCER ASSOCIATED PROTEIN

RELATED APPLICATIONS

The present application is a Continuation of PCT Application No. PCT/GB02/02782 filed Jun. 14, 2002, which in turn, claims priority from Great Britain Application Serial No. 0114643.0, filed on Jun. 15, 2001 and Great Britain Application Serial No. 0205264.5, filed on Mar. 6, 2002. Applicants claim the benefits of 35 U.S.C. § 120 as to the PCT application and priority under 35 U.S.C. § 119 as to the said Great Britain applications, and the entire disclosures of both applications are incorporated herein in their entireties.

BACKGROUND OF THE INVENTION

The present invention relates to a novel polypeptide (BCMP 101) compositions comprising the polypeptide, including vaccines, and antibodies that are immunospecific for the polypeptide. The use of the polypeptide in the diagnosis, prophylaxis and treatment of cancer, in particular breast cancer is also provided.

Breast Cancer

Breast cancer is the most frequently diagnosed non-skin cancer among women in the United States. It is second only to lung cancer in cancer-related deaths. In the UK, breast cancer is by far the commonest cancer in women, with 34,600 new cases in 1998 (Cancer Research Campaign). Ninety-nine percent of breast cancers occur in women. The risk of developing breast cancer steadily increases with age; the lifetime risk of developing breast cancer is estimated to be 1 in 8 for women in the US. The annual cost of breast cancer treatment in the United States is approximately $10 billion (Fuqua, et. al. 2000, American Association for Cancer Research, USA). Breast cancer incidence has been rising over the past five decades, but recently it has slowed. This may reflect a period of earlier detection of breast cancers by mammography. A number of established factors can increase a woman's risk of having the disease. These include older age, history of prior breast cancer, significant radiation exposure, strong family history of breast cancer, upper socioeconomic class, nulliparity, early menarche, late menopause, or age at first pregnancy greater than 30 years. Prolonged use of oral contraceptives earlier in life appears to increase risk slightly. Prolonged postmenopausal oestrogen replacement increases the risk 20 to 40%. It has been speculated that a decrease in the age at menarche, changing birth patterns, or a rise in the use of exogenous estrogens has contributed to the increase in breast cancer incidence (Fuqua, et. al. 2000, American Association for Cancer Research, USA).

Causes of Breast Cancer

Breast cancer is a heterogeneous disease. Although female hormones play a significant role in driving the origin and evolution of many breast tumours, there are a number of other recognised and unknown factors involved. Perturbations in oncogenes identified include amplification of the HER-2 and the epidermal growth factor receptor genes, and over-expression of cyclin D1. Over-expression of these oncogenes has been associated with a significantly poorer prognosis. Similarly, genetic alterations or the loss of tumour suppressor genes, such as the p53 gene, have been well documented in breast cancer and are also associated with a poorer prognosis. Researchers have identified two genes, called BRCA1 and BRCA2, which are predictive of pre-menopausal familial breast cancer. Genetic risk assessment is now possible, which may enhance the identification of candidates for chemoprevention trials (Fuqua, et al. 2000, American Association for Cancer Research, USA).

Diagnosis

Early diagnosis of breast cancer is vital to secure the most favourable outcome for treatment. Many countries with advanced healthcare systems have instituted screening programs for breast cancer. This typically takes the form of regular x-ray of the breast (mammography) during the 50-60 year old age interval where greatest benefit for this intervention has been shown. Some authorities have advocated the extension of such programs beyond 60 and to the 4049 age group. Health authorities in many countries have also promoted the importance of regular breast self-examination by women. Abnormalities detected during these screening procedures and cases presenting as symptomatic would typically be confirmed by aspiration cytology, core needle biopsy with a stereotactic or ultrasound technique for non-palpable lesions, or incisional or excisional biopsy. At the same time other information relevant to treatment options and prognosis, such as oestrogen (ER) and progesterone receptor (PR) status would typically be determined (National Cancer Institute, USA, 2000, Breast Cancer PDQ).

Disease Staging and Prognosis

Staging of breast cancer is the key to choosing the optimum treatment for each patient and to select those patients who will fare well with less intensive forms of therapy from those for whom intensive therapy is essential. Currently the process of staging involves lump and axillary lymph node biopsies, combined with extensive histopathology. Patients can be incorrectly staged with consequent over- or under-treatment. As such, there is a need for new markers that can be correlated with disease stage and used to reliably guide treatment decisions. Such new markers would not only benefit patients and health care providers by selecting the optimum treatment, but could provide significant cost and time benefits in the histology lab.

Some breast tumours become refractory to treatments, as the cancer cells develop resistance to chemotherapy drugs or lose their hormone sensitivity, leading to recurrent or metastatic disease which is often incurable. More recently, attention has focussed on the development of immunological therapies, (Green, M. C., et al. Cancer Treat. Rev. 26, 269-286 (2000); Davis, I. D., et al. Immunol. Cell Biol. 78, 179-195 (2000); Knuth, A., et al. Cancer Chemother Pharmacol. 46, S46-51 (2000); Shiku, H., et al. Cancer Chemother. Pharmacol. 46, S77-82 (2000); Saffran, D. C., et al. Cancer Metastasis Rev. 18, 437449 (1999)), such as cancer vaccines and monoclonal antibodies (mAbs), as a means of initiating and targeting a host immune response against tumour cells. In 1998 the FDA approved the use of Herceptin™ (Stebbing, J., et al. Cancer Treat. Rev. 26, 287-290 (2000); Dillman, R.O. Cancer Biother. Radiopharm. 14, 5-10 (1999); Miller, K. D., et al. Invest. New Drugs 17, 417427 (1999)), a mAb that recognises the erbB2/HER2-neu receptor protein, as a treatment for metastatic breast cancer. In combination with chemotherapy, Herceptinm™ has been shown to prolong the time to disease progression, when compared to patients receiving chemotherapy alone (Baselga, J., et al. Cancer Res. 58, 2825-2831 (1998)). Herceptinm™, however, is only effective in treating the 10-20% of patients whose tumours over-express the erbB2 protein. Thus, the identification of other suitable targets or antigens for immunotherapy of breast cancer has become increasingly important.

An ideal protein target for cancer immunotherapy should have a restricted expression profile in normal tissues and be over-expressed in tumours, such that the immune response will be targeted to tumour cells and not against other organs. In addition, the protein target should be exposed on the cell surface, where it will be accessible to therapeutic agents. Tumour antigens have been identified for a number of cancer types, by using techniques such as differential screening of cDNA (Hubert, R. S., et al. Proc. Natl. Acad, Sci. USA 96, 14523-14528 (1999); Lucas, S., et al. Int. J. Cancer 87, 55-60 (2000)), and the purification of cell-surface proteins that are recognised by tumour-specific antibodies (Catimel, B., et al. J. Biol. Chem. 271, 25664-25670 (1996)). Proteomics may be used as an alternative approach to identifying breast tumour antigens (EP 1208381, EP 1159618).

The present invention is based on the identification of a novel protein (BCMP 101) as a target for cancer therapy and diagnosis.

BCMP 101 was identified and cloned from MDA-MB468 breast cancer cell membranes. Expression of BCMP 101 in normal human tissue showed that the highest levels of expression were found in mammary, kidney and bladder tissue. Expression of BCMP 101 was elevated in kidney cancer cell lines in comparison to normal tissues. Furthermore, elevated levels of BCMP 101 gene expression were also observed in tumour tissue from a set of seven matched normal and tumour samples from breast cancer patients. The BCMP 101 sequence (FIG. 1, SEQ ID NO: 1) matches GenBank entry CAD 10629—NSE2 protein [Homo sapiens]—a Povel NS-containing protein), which was published after the priority date of this application.

SUMMARY OF THE INVENTION

Thus, the present invention provides a polypeptide which:
a) comprises or consists of the amino acid sequence shown in FIG. 1 (SEQ ID NO: 1);
b) is a derivative having one or more amino acid substitutions, modifications, deletions or insertions relative to the amino acid sequence shown in FIG. 1 (SEQ ID NO: 1); or
c) is a fragment of a polypeptide as defined in a) or b) above, which is at least ten amino acids long.

In the present application, the term "polypeptides of the invention" is used to refer to all polypeptides described in a) to c) above.

Polypeptides of the invention may be in substantially pure, isolated or recombinant form, and may be fused to other moieties. In particular, fusions of the polypeptides of the invention with localisation-reporter proteins such as the Green Fluorescent Protein (U.S. Pat. Nos. 5,625,048, 5,777,079, 6,054,321 and 5,804,387) or the DsRed fluorescent protein (Matz, M. V. et al., Nature Biotech. 17:969-973.) are specifically contemplated by the present invention. The polypeptides of the invention may be provided in substantially pure form; that is to say, they are free, to a substantial extent, from other polypeptides. Thus, a polypeptide of the invention may be provided in a composition in which it is the predominant component present (i.e. it is present at a level of at least 50%; preferably at least 75%, at least 80%, at least 85%, at least 90%, or at least 95%; when determined on a weight/weight basis excluding solvents or carriers).

In order to more fully appreciate the present invention, polypeptides within the scope of a)-c) above will now be discussed in greater detail. It will be apparent to one skilled in the art that polypeptides according to the invention include BCMP 101 (SEQ ID NO: 1), and derivatives, fragments and modified forms thereof.

Polypeptides Within the Scope of a)

A polypeptide within the scope of a), may consist of the particular amino acid sequence given in FIG. 1 (SEQ ID NO: 1) or may have an additional N-terminal and/or an additional C-terminal amino acid sequence relative to the sequence given in FIG. 1 (SEQ ID NO: 1).

Additional N-terminal or C-terminal sequences may be provided for various reasons. Techniques for providing such additional sequences are well known in the art.

Additional sequences may be provided in order to alter the characteristics of a particular polypeptide. This can be useful in improving expression or regulation of expression in particular expression systems. For example, an additional sequence may provide some protection against proteolytic cleavage. This has been done for the hormone Somatostatin by fusing it at its N-terminus to part of the β galactosidase enzyme (Itakwa et al., Science 198: 105-63 (1977)).

Additional sequences can also be useful in altering the properties of a polypeptide to aid in identification or purification. For example, a fusion protein may be provided in which a polypeptide is linked to a moiety capable of being isolated by affinity chromatography. The moiety may be an antigen or an epitope and the affinity column may comprise immobilised antibodies or immobilised antibody fragments which bind to said antigen or epitope (desirably with a high degree of specificity). The fusion protein can usually be eluted from the column by addition of an appropriate eluant.

Additional N-terminal or C-terminal sequences may, however, be present simply as a result of a particular technique used to obtain a polypeptide of the present invention and need not provide any particular advantageous characteristic to the polypeptide of the present invention. Such polypeptides are within the scope of the present invention.

Whatever additional N-terminal or C-terminal sequence is present, it is preferred that the resultant polypeptide should exhibit the immunological or biological activity of the polypeptide having the amino acid sequence shown in FIG. 1 (SEQ ID NO: 1).

Polypeptides Within the Scope of b)

Turning now to the polypeptides defined in b) above, it will be appreciated by the person skilled in the art that these polypeptides are derivatives of the polypeptide given in a) above. Such derivatives preferably exhibit the immunological or biological activity of the polypeptide having the amino acid sequence shown in FIG. 1 (SEQ ID NO: 1). It will be appreciated by one skilled in the art that derivatives can include post-translational modifications, for example but without limitation, phosphorylation, glycosylation and farnesylation.

Alterations in the amino acid sequence of a polypeptide, which do not affect the function of a polypeptide, can occur. These include amino acid deletions, insertions and substitutions and can result from alternative splicing and/or the presence of multiple translation start sites and/or stop sites. Polymorphisms may arise as a result of the infidelity of the translation process. Thus changes in amino acid sequence may be tolerated which do not affect the polypeptide's biological or immunological function.

The skilled person will appreciate that various changes can often be made to the amino acid sequence of a polypeptide which has a particular activity to produce derivatives (sometimes known as variants or "muteins") having at least a proportion of said activity, and preferably having a substantial proportion of said activity. Such derivatives of the polypeptides described in a) above are within the scope of the present invention and are discussed in greater detail below. They include allelic and non-allelic derivatives.

An example of a derivative of the polypeptide of the invention is a polypeptide as defined in a) above, apart from the substitution of one or more amino acids with one or more other amino acids. The skilled person is aware that various amino acids have similar properties. One or more such amino acids of a polypeptide can often be substituted by one or more other such amino acids without eliminating a desired activity of that polypeptide.

Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic).

Other amino acids which can often be substituted for one another include:
  phenylalanine, tyrosine and tryptophan (amino acids having aromatic side chains);
  lysine, arginine and histidine (amino acids having basic side chains);
  aspartate and glutamate (amino acids having acidic side chains);
  asparagine and glutamine (amino acids having amide side chains);
  cysteine and methionine (amino acids having sulphur-containing side chains); and
  aspartic acid and glutamic acid can substitute for phospho-serine and phospho-threonine, respectively (amino acids with acidic side chains).

Substitutions of this nature are often referred to as "conservative" or "semi-conservative" amino acid substitutions.

Amino acid deletions or insertions may also be made relative to the amino acid sequence given in a) (SEQ ID NO: 1) above. Thus, for example, amino acids which do not have a substantial effect on the biological and/or immunological activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence given in a) (SEQ ID NO: 1) above can also be made. This may be done to alter the properties of a polypeptide of the invention (e.g. to assist in identification, purification or expression, as explained above in relation to fusion proteins).

Amino acid changes relative to the sequence given in a) (SEQ ID NO: 1) above can be made using any suitable technique e.g. by using site-directed mutagenesis (Hutchinson et al., 1978, J. Biol. Chem. 253:6551).

It should be appreciated that amino acid substitutions or insertions within the scope of the present invention can be made using naturally occurring or non-naturally occurring amino acids. Whether or not natural or synthetic amino acids are used, it is preferred that only L- amino acids are present.

Whatever amino acid changes are made (whether by means of substitution, modification, insertion or deletion), preferred polypeptides of the present invention have at least 50% sequence identity with a polypeptide as defined in a) above, more preferably the degree of sequence identity is at least 75%. Sequence identities of at least 80%, at least 85%, at least 90%, at least 95%, at least 98% or at least 99% are most preferred.

The term identity can be used to describe the similarity between two polypeptide sequences. The degree of amino acid sequence identity can be calculated using a program such as "bestfit" (Smith and Waterman, Advances in Applied Mathematics, 482-489 (1981)) to find the best segment of similarity between any two sequences. The alignment is based on maximising the score achieved using a matrix of amino acid similarities, such as that described by Schwarz and Dayhof (1979) Atlas of Protein Sequence and Structure, Dayhof, M. O., Ed pp 353-358.

A software package well known in the art for carrying out this procedure is the CLUSTAL program. It compares the amino acid sequences of two polypeptides and finds the optimal alignment by inserting spaces in either sequence as appropriate. The amino acid identity or similarity (identity plus conservation of amino acid type) for an optimal alignment can also be calculated using a software package such as BLASTX. This program aligns the largest stretch of similar sequence and assigns a value to the fit. For any one pattern comparison, several regions of similarity may be found, each having a different score. One skilled in the art will appreciate that two polypeptides of different lengths may be compared over the entire length of the longer fragment. Alternatively small regions may be compared. Normally sequences of the same length are compared for a useful comparison to be made.

Where high degrees of sequence identity are present there will be relatively few differences in amino acid sequence. Thus for example they may be less than 20, less than 10, or even less than 5 differences.

Polypeptides Within the Scope of c)

As discussed supra, it is often advantageous to reduce the length of a polypeptide, provided that the resultant reduced length polypeptide still has a desired activity or can give rise to useful antibodies. Feature c) of the present invention therefore covers fragments of polypeptides a) or b) above.

The skilled person can determine whether or not a particular fragment has activity using the techniques disclosed above. Fragments are at least 10 amino acids long, preferred fragments may be at least 20, at least 30, at least 40, at least 50, at least 75 or at least 100 amino acids long. Preferably, the fragments are less than 150 amino acids long.

As will be discussed below, the polypeptides of the invention will find use in an immunotherapeutic approach to breast and/or kidney cancer. The skilled person will appreciate that for the preparation of one or more polypeptides of the invention, the preferred approach will be based on recombinant DNA techniques.

A polypeptide of the invention may be useful as antigenic material, and may be used in the production of vaccines for treatment or prophylaxis of cancer, in particular breast cancer and/or kidney cancer. Such material can be "antigenic" and/or "immunogenic". Generally, "antigenic" is taken to mean that the polypeptide is capable of being used to raise antibodies or indeed is capable of inducing an antibody response in a subject. "Immunogenic" is taken to mean that the polypeptide is capable of eliciting an immune response in a subject. Thus, in the latter case, the polypeptide may be capable of not only generating an antibody response but, in addition, non-antibody based immune responses.

It is well known that is possible to screen an antigenic polypeptide to identify epitopic regions, i.e. those regions which are responsible for the polypeptide's antigenicity or immunogenicity. Methods well known to the skilled person can be used to test fragments and/or homologues and/or derivatives for antigenicity. Thus, the fragments for use in the present invention may include one or more such epitopic regions or be sufficiently similar to such regions to retain their antigenic/immunogenic properties. Thus, for fragments for use according to the present invention the degree of identity is perhaps irrelevant, since they may be 100% identical to a particular part of a polypeptide of the invention. The key issue may be that the fragment retains the antigenic/immunogenic properties of the polypeptide from which it is derived.

Homologues, derivatives and fragments may possess at least a degree of the antigenicity/immunogenicity of the polypeptide from which they are derived.

Thus, in a further aspect, the present invention provides the use of a polypeptide of the invention in the production of a composition for the treatment or prophylaxis of cancer, particularly breast cancer and/or kidney cancer, wherein the composition is a vaccine. The vaccine optionally comprises one or more suitable adjuvants. Examples of adjuvants well-known in the art include inorganic gels, such as aluminium hydroxide, and water-in-oil emulsions, such as incomplete Freund's adjuvant. Other useful adjuvants will be well known to the skilled person.

In yet further aspects, the present invention provides:
(a) the use of a polypeptide of the invention in the preparation of an immunogenic composition, preferably a vaccine;
(b) the use of such an immunogenic composition in inducing an immune response in a subject;
(c) a method for the treatment or prophylaxis of cancer, particularly breast and/or kidney cancer in a subject, or of vaccinating a subject against cancer which comprises the step of administering to the subject an effective amount of a polypeptide of the invention, preferably as a vaccine; and
(d) a method for monitoring/assessing breast and/or kidney cancer treatment in a patient, which comprises the step of determining the presence or absence and/or quantifying at least one polypeptide, at least one nucleic acid molecule or at least one antibody of the invention in a biological sample.

As will be discussed below, the polypeptides of the invention will find use in an immunotherapeutic approach to cancer, particularly breast cancer and/or kidney cancer. The skilled person will appreciate that for the preparation of one or more such polypeptides, the preferred approach will be based on recombinant DNA techniques. In addition, nucleic acid molecules encoding the polypeptides or fragments thereof may be used in their own right.

Thus, in a further aspect, the present invention provides an isolated or recombinant nucleic acid molecule which:
d) comprises or consists of the DNA sequence shown in FIG. 1 (SEQ ID NO:2) or its RNA equivalent;
e) a sequence which codes for a derivative or fragment of a polypeptide shown in FIG. 1 (SEQ ID NO:1);
f) a sequence which is complementary to the sequences of d) or e);
g) a sequence which codes for the same polypeptide, as the sequences of d), e) or f); or
h) a sequence which shows substantial identity with any of those of d), e), f) and g).

These nucleic acid molecules are now discussed in greater detail.

The term identity can also be used to describe the similarity between two individual DNA sequences. The 'bestfit' program (Smith and Waterman, Advances in applied Mathematics, 482-489 (1981)) is one example of a type of computer software used to find the best segment of similarity between two nucleic acid sequences, whilst the GAP program enables sequences to be aligned along their whole length and finds the optimal alignment by inserting spaces in either sequence as appropriate. It is preferred if sequences which show substantial identity with any of those of d), e), f) and g) have e.g. at least 50%, at least 75%, at least 80%, at least 85%, at least 90% or 95% sequence identity.

It is preferred that if the nucleic acid molecule is a fragment of the sequence given in FIG. 1 (SEQ ID NO: 2), that it does not correspond to the following fragments: bp558-1054, bp80-565 or bp 45-547, according to the nucleotide numbering of FIG. 1 (SEQ ID NO: 2).

In a further aspect, the present invention provides a method for the prophylaxis and/or treatment of cancer, in particular breast and/or kidney cancer, in a subject, which comprises administering to said subject a therapeutically effective amount of at least one nucleic acid as defined above.

In yet another aspect, the present invention provides the use of at least one nucleic acid as defined above in the preparation of a composition for use in the prophylaxis and/or treatment of cancer, in particular breast and/or kidney cancer.

The polypeptides of the invention can be coded for by a large variety of nucleic acid molecules, taking into account the well known degeneracy of the genetic code. All of these molecules are within the scope of the present invention. They can be inserted into vectors and cloned to provide large amounts of DNA or RNA for further study. Suitable vectors may be introduced into host cells to enable the expression of polypeptides of the invention using techniques known to the person skilled in the art.

The term 'RNA equivalent' when used above indicates that a given RNA molecule has a sequence which is complementary to that of a given DNA molecule, allowing for the fact that in RNA 'U' replaces 'T' in the genetic code. The nucleic acid molecule may be in isolated, recombinant or chemically synthetic form.

Techniques for cloning, expressing and purifying polypeptides are well known to the skilled person. DNA constructs can readily be generated using methods well known in the art. These techniques are disclosed, for example in J. Sambrook et al, *Molecular Cloning* 3$^{rd}$ Edition, Cold Spring Harbour Laboratory Press (2000); in Old & Primrose Principles of Gene Manipulation 5th Edition, Blackwell Scientific Publications (1994); and in Stryer *Biochemistry* 4th *Edition*, W H Freeman and Company (1995). Modifications of DNA constructs and the polypeptides expressed such as the addition of promoters, enhancers, signal sequences, leader sequences, translation start and stop signals and DNA stability controlling regions, or the addition of fusion partners may then be facilitated.

Normally the DNA construct will be inserted into a vector, which may be of phage or plasmid origin. Expression of the polypeptide is achieved by the transformation or transfection of the vector into a host cell which may be of eukaryotic or prokaryotic origin. Such vectors and suitable host cells form additional aspects of the present invention.

The nucleotides of the present invention, including DNA and RNA, and comprising a sequence encoding a polypeptide of the invention, may be synthesised using methods known in the art, such as using conventional chemical approaches or polymerase chain reaction (PCR) amplification. The nucleotides of the present invention also permit the identification and cloning of the gene encoding a polypeptide as defined herein from any species, for instance by screening cDNA libraries, genomic libraries or expression libraries.

Knowledge of the nucleic acid structure can be used to raise antibodies and for gene therapy. Techniques for this are well-known by those skilled in the art, as discussed in more detail herein.

By using appropriate expression systems, polypeptides of the invention may be expressed in glycosylated or non-glycosylated form. Non-glycosylated forms can be produced by expression in prokaryotic hosts, such as E. coli.

Polypeptides comprising N-terminal methionine may be produced using certain expression systems, whilst in others the mature polypeptide will lack this residue. Preferred techniques for cloning, expressing and purifying a polypeptide of the invention are summarised below:

Polypeptides may be prepared under native or denaturing conditions and then subsequently refolded. Baculoviral expression vectors include secretory plasmids (such as pACGP67 from Pharmingen), which may have an epitope tag sequence cloned in frame (e.g. myc, V5 or His) to aid detection and allow for subsequent purification of the polypeptide. Mammalian expression vectors may include pCDNA3 and pSecTag (both Invitrogen), and pREP9 and pCEP4 (Invitrogen). E. coli systems include the pBad series (His tagged—Invitrogen) or pGex series (Pharmacia).

In addition to nucleic acid molecules coding for polypeptides of the invention, referred to herein as "coding" nucleic acid molecules, the present invention also includes complementary nucleic acid molecules. Thus, for example, both strands of a double stranded nucleic acid molecule are included within the scope of the present invention (whether or not they are associated with one another). Also included are mRNA molecules and complementary DNA Molecules (e.g. cDNA molecules).

Nucleic acid molecules which can hybridise to any of the nucleic acid molecules discussed above are also covered by the present invention. Such nucleic acid molecules are referred to herein as "hybridising" nucleic acid molecules. Hybridising nucleic acid molecules can be useful as probes or primers, for example.

Desirably such hybridising molecules are at least 10 nucleotides in length and preferably are at least 25 or at least 50 nucleotides in length. The hybridising nucleic acid molecules preferably hybridise to nucleic acids within the scope of d) (SEQ ID NO: 2), e), f), g) or h) above specifically.

Desirably the hybridising molecules will hybridise to such molecules under stringent hybridisation conditions. One example of stringent hybridisation conditions is where attempted hybridisation is carried out at a temperature of from about 35° C. to about 65° C. using a salt solution which is about 0.9 molar. However, the skilled person will be able to vary such conditions as appropriate in order to take into account variables such as probe length, base composition, type of ions present, etc. For a high degree of selectivity, relatively stringent conditions are used to form the duplexes, such as low salt or high temperature conditions. As used herein, "highly stringent conditions" means hybridisation to filter-bound DNA in 0.5 M NaHPO$_4$, 7% sodium dodecyl sulphate (SDS), 1 mM EDTA at 65° C., and washing in 0.1×SSC/0.1% SDS at 68° C. (Ausubel F. M. et al., eds., 1989, Current Protocols in Molecular Biology, Vol. 1, Green Publishing Associates, Inc., and John Wiley & Sons, Inc., New York, at p. 2.10.3). For some applications, less stringent conditions for duplex formation are required. As used herein "moderately stringent conditions" means washing in 0.2× SSC/0.1% SDS at 42° C. (Ausubel et al., 1989, supra). Hybridisation conditions can also be rendered more stringent by the addition of increasing amounts of formamide, to destabilise the hybrid duplex. Thus, particular hybridisation conditions can be readily manipulated, and will generally be chosen depending on the desired results. In general, convenient hybridisation temperatures in the presence of 50% formamide are: 42° C. for a probe which is 95 to 100% identical to the fragment of a gene encoding a polypeptide as defined herein, 37° C. for 90 to 95% identity and 32° C. for 70 to 90% identity. In the preparation of genomic libraries, DNA fragments are generated, some of which will encode parts or the whole of a polypeptide as defined herein. The DNA may be cleaved at specific sites using various restriction enzymes. Alternatively, one may use DNAse in the presence of manganese to fragment the DNA, or the DNA can be physically sheared, as for example, by sonication. The DNA fragments can then be separated according to size by standard techniques, including but not limited to agarose and polyacrylamide gel electrophoresis, column chromatography and sucrose gradient centrifugation. The DNA fragments can then be inserted into suitable vectors, including but not limited to plasmids, cosmids, bacteriophages lambda or T$_4$, and yeast artificial chromosomes (YACs). (See, for example, Sambrook et al., 2000, *Molecular Cloning*, A Laboratory Manual, 3$^{rd}$ Ed., Cold Spring Harbor Laboratory Press, Cold Spring Harbor, N.Y.; Glover, D. M. (ed.), 1985, *DNA Cloning: A Practical Approach*, MRL Press, Ltd., Oxford, U.K. Vol. 1, II; Ausubel F. M. et al., eds., 1989, Current Protocols in Molecular Biology, Vol. I, Green Publishing Associates, Inc., and John Wiley & sons, Inc., New York). The genomic library may be screened by nucleic acid hybridisation to labelled probe (Benton & Davis, 1977, *Science* 196:180; Grunstein & Hogness, 1975, *Proc. Natl. Acad. Sci. U.S.A.* 72:3961).

Manipulation of the DNA encoding a polypeptide is a particularly powerful technique for both modifying proteins and for generating large quantities of protein for purification purposes. This may involve the use of PCR techniques to amplify a desired nucleic acid sequence. Thus the sequence data provided herein can be used to design primers for use in PCR so that a desired sequence can be targeted and then amplified to a high degree.

Typically, primers will be at least five nucleotides long and will generally be at least ten nucleotides long (e.g. fifteen to twenty-five nucleotides long). In some cases, primers of at least thirty or at least thirty-five nucleotides in length may be used.

As a further alternative chemical synthesis may be used. This may be automated. Relatively short sequences may be chemically synthesised and ligated together to provide a longer sequence.

In addition to being used as primers and/or probes, hybridising nucleic acid molecules of the present invention can be used as anti-sense molecules to alter the expression of polypeptides of the present invention by binding to complementary nucleic acid molecules. This technique can be used in anti-sense therapy.

As used herein, an "antisense" nucleic acid refers to a nucleic acid capable of hybridising by virtue of some sequence complementarity to a portion of an RNA (preferably mRNA) encoding a polypeptide of the invention. The antisense nucleic acid may be complementary to a coding and/or non-coding region of a mRNA encoding a polypeptide of the invention. Such antisense nucleic acids have utility as compounds that inhibit expression, and can be used in the treatment or prevention of cancer, in particular breast cancer and/or kidney cancer.

In a specific embodiment, expression of a polypeptide of the invention is inhibited by use of antisense nucleic acids. The present invention provides the therapeutic or prophylactic use of nucleic acids comprising at least six nucleotides that are antisense to a gene or cDNA encoding a polypeptide of the invention.

A hybridising nucleic acid molecule of the present invention may have a high degree of sequence identity along its length with a nucleic acid molecule within the scope of d)-h) above (e.g. at least 50%, at least 75%, at least 80%, at least 85% or at least 90% or 95% sequence identity). As will be appreciated by the skilled person, the higher the sequence identity a given single stranded nucleic acid molecule has with another nucleic acid molecule, the greater the likelihood that it will hybridise to a nucleic acid molecule which is complementary to that other nucleic acid molecule under appropriate conditions.

In view of the foregoing description the skilled person will appreciate that a large number of nucleic acids are within the scope of the present invention. Unless the context indicates otherwise, nucleic acid molecules of the present invention may have one or more of the following characteristics:

1) they may be DNA or RNA;
2) they may be single or double stranded;
3) they may be provided in recombinant form, e.g. covalently linked to a 5' and/or a 3' flanking sequence to provide a molecule which does not occur in nature;
4) they may be provided without 5' and/or 3' flanking sequences which normally occur in nature;
5) they may be provided in substantially pure form. Thus they may be provided in a form which is substantially free from contaminating proteins and/or from other nucleic acids; and
6) they may be provided with introns or without introns (e.g. as cDNA).

If desired, a gene encoding a polypeptide of the invention, a related gene, or related nucleic acid sequences or subsequences, including complementary sequences, can also be used in hybridisation assays. A nucleotide encoding a polypeptide of the invention, or subsequences thereof comprising at least 8 nucleotides, can be used as a hybridisation probe. Hybridisation assays can be used for detection, prognosis, diagnosis, or monitoring of conditions, disorders, or disease states, associated with aberrant expression of genes encoding a polypeptide as defined herein, or for differential diagnosis of patients with signs or symptoms suggestive of cancer, in particular breast cancer and/or kidney cancer. In particular, such a hybridisation assay can be carried out by a method comprising contacting a patient sample containing nucleic acid with a nucleic acid probe capable of hybridising to a DNA or RNA that encodes a polypeptide of the invention, under conditions such that hybridisation can occur, and detecting or measuring any resulting hybridisation. Nucleotides can be used for therapy of patients having cancer, in particular breast cancer and/or kidney cancer, as described below.

In another embodiment, a preparation of oligonucleotides comprising 10 or more consecutive nucleotides complementary to a nucleotide sequence encoding a polypeptide of the invention or fragment thereof for use as vaccines for the treatment of cancer, in particular breast cancer and/or kidney cancer. Such preparations may include adjuvants or other vehicles.

In a specific embodiment, nucleic acids comprising a sequence encoding a polypeptide of the invention, are administered to promote polypeptide function by way of gene therapy. Gene therapy refers to administration to a subject of an expressed or expressible nucleic acid. In this embodiment, the nucleic acid produces its encoded protein that mediates a therapeutic effect by promoting polypeptide function. Any of the methods for gene therapy available in the art can be used according to the present invention.

In a preferred aspect, the compound comprises a nucleic acid of the invention, such as a nucleic acid encoding a polypeptide of the invention, said nucleic acid being part of an expression vector that expresses a polypeptide of the invention in a suitable host. In particular, such a nucleic acid has a promoter operably linked to the polypeptide coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller & Smithies, 1989, Proc. Natl. Acad. Sci. USA 86:8932-8935; Zijlstra et al., 1989, Nature 342:435438).

Delivery of the nucleic acid into a patient may be direct, in which case the patient is directly exposed to the nucleic acid or nucleic acid-carrying vector; this approach is known as in vivo gene therapy. Alternatively, delivery of the nucleic acid into the patient may be indirect, in which case cells are first transformed with the nucleic acid in vitro and then transplanted into the patient; this approach is known as ex vivo gene therapy.

As described herein, BCMP 101 is associated with cancer, in particular breast and kidney cancer and as such provides a means of detection/diagnosis. Thus, in another aspect, the present invention provides a method of screening for and/or diagnosis of cancer, in particular breast cancer and/or kidney cancer in a subject which comprises the step of detecting and/or quantifying the amount of a polypeptide or nucleic acid molecule of the invention in a biological sample obtained from said subject. In a further embodiment, antibodies which recognise the polypeptides of the invention are used to detect the amount of a polypeptide as described herein in a biological sample.

In one embodiment, binding of antibody in tissue sections can be used to detect aberrant polypeptide localisation or an aberrant level of polypeptide. In a specific embodiment, antibody to a polypeptide of the invention can be used to assay a patient tissue (e.g., a breast biopsy) for the level of the polypeptide where an aberrant level of polypeptide is indicative of cancer, in particular breast cancer and/or kidney cancer. As used herein, an "aberrant level" means a level that is increased compared with the level in a subject free from cancer or a reference level.

Suitable immunoassays include, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

In another aspect, the present invention provides a method for the prophylaxis and/or treatment of cancer, in particular breast cancer and/or kidney cancer, in a subject, which comprises administering to said subject a therapeutically effective amount of an antibody which binds to at least one polypeptide of the invention.

A convenient means for such detection/quantifying will involve the use of antibodies. Thus, the polypeptides of the invention also find use in raising antibodies. Thus, in a further aspect, the present invention provides antibodies, which bind to a polypeptide of the invention and the use of these antibodies in the preparation of a composition for use in the prophylaxis and/or treatment of cancer in particular breast cancer and/or kidney cancer. In particular, the preparation of vaccines and/or compositions comprising or consisting of antibodies is a preferred embodiment of this aspect of the invention.

Preferred antibodies bind specifically to polypeptides of the present invention so that they can be used to purify and/or inhibit the activity of such polypeptides.

Thus, the polypeptide of the invention, may be used as an immunogen to generate antibodies which immunospecifically bind such an immunogen. Antibodies of the invention include, but are not limited to polyclonal, monoclonal, bispecific, humanised or chimeric antibodies, single chain antibodies, Fab fragments and F(ab') fragments, fragments produced by a Fab expression library, anti-idiotypic (anti-Id) antibodies, and epitope-binding fragments of any of the above. The term "antibody" as used herein refers to immunoglobulin molecules and immunologically active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

In the production of antibodies, screening for the desired antibody can be accomplished by techniques known in the art, e.g. ELISA (enzyme-linked immunosorbent assay). For example, to select antibodies which recognise a specific domain of a polypeptide of the invention, one may assay generated hybridomas for a product which binds to a polypeptide fragment containing such domain. For selection of an antibody that specifically binds a first polypeptide homologue but which does not specifically bind to (or binds less avidly to) a second polypeptide homologue, one can select on the basis of positive binding to the first polypeptide homologue and a lack of binding to (or reduced binding to) the second polypeptide homologue.

For preparation of monoclonal antibodies (mAbs) directed toward a polypeptide of the invention, any technique which provides for the production of antibody molecules by continuous cell lines in culture may be used. For example, the hybridoma technique originally developed by Kohler and Milstein (1975, Nature 256:495497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, mAbs can be produced in germ-free animals utilising known technology (PCT/US90/02545).

The mAbs include but are not limited to human mAbs and chimeric mAbs (e.g., human-mouse chimeras). A chimeric antibody is a molecule in which different portions are derived from different animal species, such as those having a human immunoglobulin constant region and a variable region derived from a murine mAb. (See, e.g., U.S. Pat. No. 4,816,567; and U.S. Pat. No. 4,816,397) Humanised antibodies are antibody molecules from non-human species having one or more complementarity determining regions (CDRs) from the non-human species and a framework region from a human immunoglobulin molecule. (See, e.g., U.S. Pat. No. 5,585,089).

Chimeric and humanised mAbs can be produced by recombinant DNA techniques known in the art, for example using methods described in WO 87/02671; EP 184,187; EP 171,496; EP 173,494; WO 86/01533; U.S. Pat. No. 4,816,567; EP 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunised in the normal fashion with a selected antigen, e.g., all or a portion of a polypeptide of the invention. mAbs directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human mAbs and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

Completely human antibodies which recognise a selected epitope can be generated using a technique referred to as "guided selection". In this approach a selected non-human mAb, e.g., a mouse antibody, is used to guide the selection of a completely human antibody recognising the same epitope. (Jespers et al. (1994) Bio/technology 12:899-903).

The antibodies of the present invention can also be generated using various phage display methods known in the art. In phage display methods, functional antibody domains are displayed on the surface of phage particles which carry the polynucleotide sequences encoding them. In particular, such phage can be utilised to display antigen-binding domains expressed from a repertoire or combinatorial antibody library (e.g., human or murine). Phage expressing an antigen binding domain that binds the antigen of interest can be selected or identified with antigen, e.g., using labelled antigen or antigen bound or captured to a solid surface or bead. Phage used in these methods are typically filamentous phage including fd and M13 binding domains expressed from phage with Fab, Fv or disulphide stabilised Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184: 177-186 (1995); Kettleborough et al., Eur. J. Immunol. 24:952-958 (1994); Persic et al., Gene 187 9-18 (1997) Burton et al., Advances in Immunology 57:191-280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in WO 92/22324; Mullinax et al., BioTechniques 12(6):864-869 (1992); and Sawai et al., AJRI 34:26-34 (1995); and Better et al., Science 240:1041-1043 (1988).

Examples of techniques which can be used to produce single-chain Fvs and antibodies include those described in U.S. Pat. No. 4,946,778 and U.S. Pat. No. 5,258,498; Huston et al., Methods in Enzymology 203:46-88 (1991); Shu et al., PNAS 90:7995-7999 (1993); and Skerra et al., Science 240:1038-1040 (1988).

The invention further provides for the use of bispecific antibodies, which can be made by methods known in the art. Traditional production of full-length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details for generating bispecific antibodies see, for example, Suresh et al., Methods in Enzymology, 1986, 121:210.

The invention provides functionally active fragments, derivatives or analogs of the anti-polypeptide immunoglobulin molecules. "Functionally active" means that the fragment, derivative or analogue is able to elicit anti-anti-idiotype antibodies (i.e., tertiary antibodies) that recognise the same antigen that is recognised by the antibody from which the fragment, derivative or analogue is derived. Specifically, in a preferred embodiment the antigenicity of the idiotype of the immunoglobulin molecule may be enhanced by deletion of framework and CDR sequences that are C-terminal to the CDR sequence that specifically recognises the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')2 fragments and Fab fragments. Antibody fragments which recognise specific epitopes may be generated by known techniques. F(ab')2 fragments consist of the variable region, the light chain constant region and the CH1 domain of the heavy chain and are generated by pepsin digestion of the antibody molecule. Fab fragments are generated by reducing the disulphide bridges of the $F(ab')_2$ fragments. The invention also provides heavy chain and light chain dimers of the antibodies of the invention, or any minimal fragment thereof such as Fvs or single chain antibodies (SCAs) (e.g., as described in U.S. Pat. No. 4,946,778; Bird, 1988, Science 242:42342; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion polypeptides of the immunoglobulins of the invention (or functionally active fragments thereof), for example in which the immunoglobulin is fused via a covalent bond (e.g., a peptide bond), at either the N-terminus or the C-terminus to an amino acid sequence of another polypeptide (or portion thereof, preferably at least 10, 20 or 50 amino acid portion of the polypeptide) that is not the immunoglobulin. Preferably the immunoglobulin, or fragment thereof, is covalently linked to the other polypeptide at the N-terminus of the constant domain. As stated above, such fusion polypeptides may facilitate purification, increase half-life in vivo, and enhance the delivery of an antigen across an epithelial barrier to the immune system.

The immunoglobulins of the invention include analogues and derivatives that are either modified, i.e., by the covalent attachment of any type of molecule as long as such covalent attachment that does not impair immunospecific binding.

For example, but not by way of limitation, the derivatives and analogues of the immunoglobulins include those that have been further modified, e.g., by glycosylation, acetylation, pegylation, phosphylation, amidation, derivatisation by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analogue or derivative may contain one or more non-classical amino acids.

The foregoing antibodies can be used in methods known in the art relating to the localisation and activity of the polypeptides of the invention, e.g., for imaging or radioimaging these polypeptides, measuring levels thereof in appropriate biological samples, in diagnostic methods, etc. and for radiotherapy.

The antibodies of the invention can be produced by any method known in the art for the synthesis of antibodies, in particular, by chemical synthesis or by recombinant expression, and are preferably produced by recombinant expression technique.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesised oligonucleotides (e.g., as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognises a particular antigen is not available (or a source for a cDNA library for cloning a nucleic acid encoding such an antibody), antibodies specific for a particular antigen may be generated by any method known in the art, for example, by immunising an animal, such as a rabbit, to generate polyclonal antibodies or, more preferably, by generating monoclonal antibodies. Alternatively, a clone encoding at least the Fab portion of the antibody may be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g., WO 86/05807; WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulphide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCR based methods, etc.

In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanised antibodies.

Once a nucleic acid encoding an antibody of the invention has been obtained, the vector for the production of the antibody may be produced by recombinant DNA technology using techniques well known in the art. Thus, methods for preparing the polypeptides of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, 2d Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *E. coli*, or, preferably, eukaryotic cells, especially for the expression of whole recombinant antibody molecule. In particular, mammalian cells such as Chinese hamster ovary cells (CHO); in conjunction with a vector such as the major intermediate early gene promoter element from human cytomegalovirus is an effective expression system for antibodies (Foecking et al., 1986, Gene 45: 101; Cockett et al., 1990, Bio/Technology 8:2).

A variety of host-expression vector systems may be utilised to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, HEK 293, 3T3 cells) harbouring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a polypeptide is to be produced, for the generation of pharmaceutical compositions comprising an antibody molecule, vectors which direct the expression of high levels of fusion polypeptide products that are readily purified may be desirable. Such vectors include, but are not limited, to the E. coli expression vector pUR278 (Ruther et al., 1983, EMBO J. 2:1791), in which the antibody coding sequence may be ligated individually into the vector in frame with the lac Z coding region so that a fusion polypeptide is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion polypeptides with glutathione S-transferase (GST). In general, such fusion polypeptides are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) may be utilised.

As discussed above, a host cell strain may be chosen which modulates the expression of the inserted sequences, or modifies and processes the gene product in the specific fashion desired. Such modifications (e.g., glycosylation) and processing (e.g., cleavage) of polypeptide products may be important for the function of the polypeptide.

For long-term, high-yield production of recombinant antibodies, stable expression is preferred. For example, cells lines that stably express an antibody of interest can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines may be particularly useful in screening and evaluation of agents that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of polypeptides.

Alternatively, any fusion polypeptide may be readily purified by utilising an antibody specific for the fusion polypeptide being expressed. For example, a system described by Janknecht et al. allows for the ready purification of non-denatured fusion polypeptides expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion polypeptide. Extracts from cells infected with recombinant vaccinia virus are loaded onto $Ni^{2+}$ nitriloacetic acid-agarose columns and histidine-tagged proteins are selectively eluted with imidazole-containing buffers.

In a preferred embodiment, antibodies of the invention or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and $^{99}Tc$.

Antibodies of the invention or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a polypeptide such as tumour necrosis factor, α-interferon, β-interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described in U.S. Pat. No. 4,676,980.

An antibody with or without a therapeutic moiety conjugated to it can be used as a therapeutic that is administered alone or in combination with cytotoxic factor(s) and/or cytokine(s).

Polyclonal antibodies can be raised by stimulating their production in a suitable animal host (e.g. a chicken, mouse, rat, guinea pig, rabbit, sheep, goat or monkey) when the polypeptide of the present invention is injected into the animal. If necessary, an adjuvant may be administered together with the polypeptide of the invention. The antibodies can then be purified by virtue of their binding to a polypeptide of the invention.

Monoclonal antibodies can be produced from hybridomas. These can be formed by fusing myeloma cells and spleen cells which produce the desired antibody in order to form an immortal cell line. This is the well known Kohler & Milstein technique (*Nature* 256 52-55 (1975)).

A further aspect of the invention provides methods of screening for agents that modulate (e.g., upregulate or downregulate) a characteristic of, e.g., the expression or the enzymatic or binding activity, of a polypeptide of the invention.

The invention provides methods for identifying active agents (e.g., chemical compounds, proteins, or peptides) that bind to a polypeptide of the invention and/or have a stimulatory or inhibitory effect on the expression or activity of a polypeptide of the invention. Examples of candidate agents, include, but are not limited to, nucleic acids (e.g., DNA and RNA), carbohydrates, lipids, proteins, peptides, peptidomimetics, agonists, antagonists, small molecules and other drugs. Active agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683)

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g., presented in solution (e.g., Houghten, 1992, Bio/Techniques 13:412421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403, 484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

In one embodiment, agents that interact with (i.e., bind to) a polypeptide of the invention are identified in a cell-based assay system. In accordance with this embodiment, cells expressing a polypeptide of the invention are contacted with a candidate agent or a control agent and the ability of the candidate agent to interact with said polypeptide is determined. If desired, this assay may be used to screen a plurality (e.g. a library) of candidate agents. The cell, for example, can be of prokaryotic origin (e.g., *E. coli*) or eukaryotic origin (e.g., yeast or mammalian). Further, the cells can express the polypeptide of the invention endogenously or be genetically engineered to express said polypeptide. In some embodiments, the polypeptide of the invention or the candidate agent is labelled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a polypeptide and a candidate agent. The ability of the candidate agent to interact directly or indirectly with the polypeptide of the invention can be determined by methods known to those of skill in the art. For example, but without limitation, the interaction between a candidate agent and a polypeptide of the invention can be determined by flow cytometry, a scintillation assay, immunoprecipitation or western blot analysis.

In another embodiment, agents that interact with (i.e., bind to) a polypeptide of the invention are identified in a cell-free assay system. In accordance with this embodiment, a native or recombinant polypeptide of the invention is contacted with a candidate agent or a control agent and the ability of the candidate agent to interact with said polypeptide is determined. If desired, this assay may be used to screen a plurality (e.g. a library) of candidate agents. Preferably, the polypeptide is first immobilised, by, for example, contacting the polypeptide with an immobilised antibody which specifically recognises and binds it, or by contacting a purified preparation of polypeptide with a surface designed to bind proteins. The polypeptide may be partially or completely purified (e.g., partially or completely free of other polypeptides) or part of a cell lysate. Further, the polypeptide may be a fusion polypeptide comprising the polypeptide of the invention and a domain such as glutathionine-S-transferase. Alternatively, the polypeptide can be biotinylated using techniques well known to those of skill in the art (e.g., biotinylation kit, Pierce Chemicals; Rockford, Ill.). The ability of the candidate agent to interact with the polypeptide can be can be duplicated by methods known to those of skill in the art.

In another embodiment, a cell-based assay system is used to identify active agents that bind to and/or modulate the activity of a protein, such as an enzyme, or a biologically active portion thereof, which is responsible for the production or degradation of the polypeptide of the invention or is responsible for the post-translational modification of the polypeptide. In a primary screen, a plurality (e.g., a library) of agents are contacted with cells that naturally or recombinantly express: (i) a polypeptide of the invention; and (ii) a protein that is responsible for processing of the polypeptide in order to identify compounds that modulate the production, degradation, or post-translational modification of the polypeptide. If desired, active agents identified in the primary screen can then be assayed in a secondary screen against cells naturally or recombinantly expressing the specific polypeptide of interest. The ability of the candidate agent to modulate the production, degradation or post-translational modification of a polypeptide can be determined by methods known to those of skill in the art, including without limitation, flow cytometry, a scintillation assay, immunoprecipitation and western blot analysis.

In another embodiment, agents that competitively interact with a polypeptide of the invention are identified in a competitive binding assay. In accordance with this embodiment, cells expressing the polypeptide are contacted with a candidate agent and as agent known to interact with the polypeptide; the ability of the candidate agent to competitively interact with the polypeptide is then determined. Alternatively, agents that competitively interact with a polypeptide of the invention are identified in a cell-free assay system by contacting said polypeptide with a candidate agent and an agent known to interact with the polypeptide. As stated above, the ability of the candidate agent to interact with a polypeptide of the invention can be determined by methods known to those of skill in the art. These assays, whether cell-based or cell-free, can be used to screen a plurality (e.g., a library) of candidate agents.

In another embodiment, agents that modulate (i.e., upregulate or down-regulate) the expression of a polypeptide of the invention are identified by contacting cells (e.g., cells of prokaryotic origin or eukaryotic origin) expressing the polypeptide with a candidate agent or a control agent (e.g., phosphate buffered saline (PBS)) and determining the expression of the polypeptide, or mRNA encoding the polypeptide. The level of expression of a selected polypeptide, or mRNA encoding polypeptide, in the presence of the candidate agent is compared to the level of expression of the polypeptide or mRNA encoding the polypeptide in the absence of the candidate agent (e.g., in the presence of a control agent). The candidate agent can then be identified as a modulator of the expression of the polypeptide based on this comparison. For example, when expression of the polypeptide, or mRNA encoding the polypeptide, is significantly greater in the presence of the candidate agent than in its absence, the candidate agent is identified as a stimulator of expression of the polypeptide, or mRNA encoding the polypeptide. Alternatively, when expression of the polypeptide, or mRNA encoding the polypeptide, is significantly less in the presence of the candidate agent than in its absence, the candidate agent is identified as an inhibitor of the expression of the polypeptide or mRNA encoding the polypeptide. The level of expression of a polypeptide of the invention or the mRNA that encodes it can be determined by methods known to those of skill in the art based on the present description. For example, mRNA expression can be assessed by Northern blot analysis or RT-PCR, and protein levels can be assessed by western blot analysis.

In another embodiment, active agents that modulate the activity of a polypeptide of the invention are identified by contacting a preparation containing the polypeptide, or cells (e.g., prokaryotic or eukaryotic cells) expressing the polypeptide with a candidate agent or a control agent and determining the ability of the candidate agent to modulate (e.g., stimulate or inhibit) the activity of polypeptide. The activity of a polypeptide can be assessed by detecting its effect on a "downstream effector" for example, but without limitation, induction of a cellular signal transduction pathway of the polypeptide, detecting catalytic or enzymatic activity of the target on a suitable substrate, detecting the induction of a reporter gene (e.g., a regulatory element that is responsive to a polypeptide of the invention and is operably linked to a nucleic acid encoding a detectable marker, e.g., luciferase), or detecting a cellular response, for example, cellular differentiation, or cell proliferation as the case may be, based on the present description, techniques known to those of skill in the art can be used for measuring these activities (see, e.g., U.S. Pat. No. 5,401,639). The candidate agent can then be identified as a modulator of the activity of a polypeptide of the invention by comparing the effects of the candidate agent to the control agent. Suitable control agents include phosphate buffered saline (PBS) and normal saline (NS).

In another embodiment, active agents that modulate (i.e., upregulate or downregulate) the expression, activity or both the expression and activity of a polypeptide of the invention are identified in an animal model. Examples of suitable animals include, but are not limited to, mice, rats, rabbits, monkeys, guinea pigs, dogs and cats. Preferably, the animal used represents a model of breast cancer and/or kidney cancer. In accordance with this embodiment, the candidate agent or a control agent is administered (e.g., orally, rectally or parenterally such as intraperitoneally or intravenously) to a suitable animal and the effect on the expression, activity or both expression and activity of the polypeptide is determined. Changes in the expression of a polypeptide can be assessed by any suitable method described above, based on the present description.

In yet another embodiment, a polypeptide of the invention is used as a "bait protein" in a two-hybrid assay or three-hybrid assay to identify other proteins that bind to or interact with the polypeptide (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and WO 94/10300). As those skilled in the art will appreciate, such binding proteins are also likely to be involved in the propagation of signals by the polypeptides of the invention as, for example, upstream or downstream elements of a signalling pathway involving the polypeptides of the invention.

Thus, the present invention provides assays for use in drug discovery in order to identify or verify the efficacy of agents for treatment or prevention of cancer, in particular breast cancer and/or kidney cancer. Candidate agents can be assayed for their ability to modulate levels of a polypeptide of the invention, in a subject having breast cancer and/or kidney cancer. Active agents able to modulate levels of a polypeptide of the invention in a subject having breast cancer and/or kidney cancer towards levels found in subjects free from breast cancer and/or kidney cancer, or to produce similar changes in experimental animal models of breast cancer and/or kidney cancer, can be used as lead agents for further drug discovery, or used therapeutically. Expression of a polypeptide of the invention can be assayed by, for example, immunoassays, gel electrophoresis followed by visualization, detection of activity, or any other method taught herein or known to those skilled in the art. Such assays can be used to screen candidate drugs, in clinical monitoring or in drug development, where abundance of a polypeptide of the invention can serve as a surrogate marker for clinical disease.

One skilled in the art will also appreciate that a polypeptide of the invention above may be used in a method for the structure-based design of an agent, in particular a small molecule which acts to modulate (e.g. stimulate or inhibit) the activity of said polypeptide, said method comprising:
1) determining the three-dimensional structure of said polypeptide;
2) deducing the three-dimensional structure of the likely reactive or binding site(s) of the agent;
3) synthesizing candidate agents that are predicted to react or bind to the deduced reactive or binding site; and
4) testing whether the candidate agent is able to modulate the activity of said polypeptide.

It will be appreciated that the method described above is likely to be an iterative process.

This invention further provides novel active agents identified by the above-described screening methods and uses thereof for treatments as described herein.

As used herein, the term "active agent" refers to the polypeptides of the invention and nucleic acid molecules encoding the polypeptides, antibodies against the polypeptides and agents which modulate the expression and/or activity of the polypeptides of the invention. Preferably, the active agent is a small molecule.

As discussed herein, active agents of the invention find use in the treatment or prophylaxis of breast and/or kidney cancer.

Thus, in an additional aspect, the present invention provides a pharmaceutical composition comprising at least one active agent of the invention, optionally together with one or more pharmaceutically acceptable excipients, carriers or diluents. In one aspect, the pharmaceutical composition is for use as a vaccine and so any additional components will be acceptable for vaccine use. In addition, the skilled person will appreciate that one or more suitable adjuvants may be added to such vaccine preparations.

The composition will usually be supplied as part of a sterile, pharmaceutical composition which will normally include a pharmaceutically acceptable carrier. This pharmaceutical composition may be in any suitable form, (depending upon the desired method of administering it to a patient).

It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions).

Suitable excipients for tablets or hard gelatine capsules include lactose, maize starch or derivatives thereof, stearic acid or salts thereof.

Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions, oils (e.g. vegetable oils) may be used to provide oil-in-water or water-in-oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3(6):318 (1986).

Pharmaceutical compositions adapted for topical administration may be formulated as ointments, creams, suspensions, lotions, powders, solutions, pastes, gels, sprays, aerosols or oils. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solution which may contain anti-oxidants, buffers, bacteriostats and solutes which render the composition substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilised) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colorants, odorants, salts (polypeptides of the present invention may themselves be provided in the form of a pharmaceutically acceptable salt), buffers, coating agents or antioxidants. They may also contain therapeutically active agents in addition to the polypeptide of the present invention.

Dosages of the active agent of the present invention can vary between wide limits, depending upon the disease or disorder to be treated, the age and condition of the individual to be treated, etc. and a physician will ultimately determine appropriate dosages to be used. This dosage may be repeated as often as appropriate. If side effects develop the amount and/or frequency of the dosage can be reduced, in accordance with normal clinical practice.

In a further aspect, the present invention provides a method for the prophylaxis and/or treatment of breast and/or kidney cancer in a subject, which comprises administering to said subject a therapeutically effective amount of at least active agent of the invention.

In another aspect, the present invention provides the use of at least one polypeptide or fragment thereof, nucleic acid molecule or antibody of the invention in the preparation of a medicament for use in the prophylaxis and/or treatment of breast and/or kidney cancer. In particular, the preparation of vaccines and/or compositions comprising or consisting of antibodies is a preferred embodiment of this aspect of the invention.

In the context of the present invention, the biological sample can be obtained from any source, such as a serum sample or a tissue sample, e.g. breast or kidney tissue. When looking for evidence of metastasis, one would look at major sites of breast metastasis such as lymph nodes, liver, lung and/or bone and of kidney metastasis, such as lymph nodes, lung and/or bone.

Preferred features of each aspect of the invention are as for each of the other aspects *mutatis mutandis*. The prior art documents mentioned herein are incorporated by reference to the fullest extent permitted by law.

The invention will now be described with reference to the following examples, which should not in any way be construed as limiting the scope of the present invention. The examples refer to the figures in which:

FIG. 1: shows the predicted amino acid sequence (SEQ ID NO: 1) and the nucleic acid sequence (SEQ ID NO: 2) of BCMP 101. The tandem mass spectrum is in bold and italicised. MALDI mass spectra are in bold and underlined. The peptide sequence used to raise the polyclonal antibody against BCMP 101 is shaded.

FIG. 2: shows tissue distribution of BCMP 101 mRNA. Levels of mRNA in normal tissues (including kidney) and two kidney cancer cell lines (Wilm's tumour cell line G401 and human embryonic kidney cell line 293) were quantified by real time RT-PCR. mRNA levels are expressed as the number of copies ng$^{-1}$ cDNA.

Figure 3:
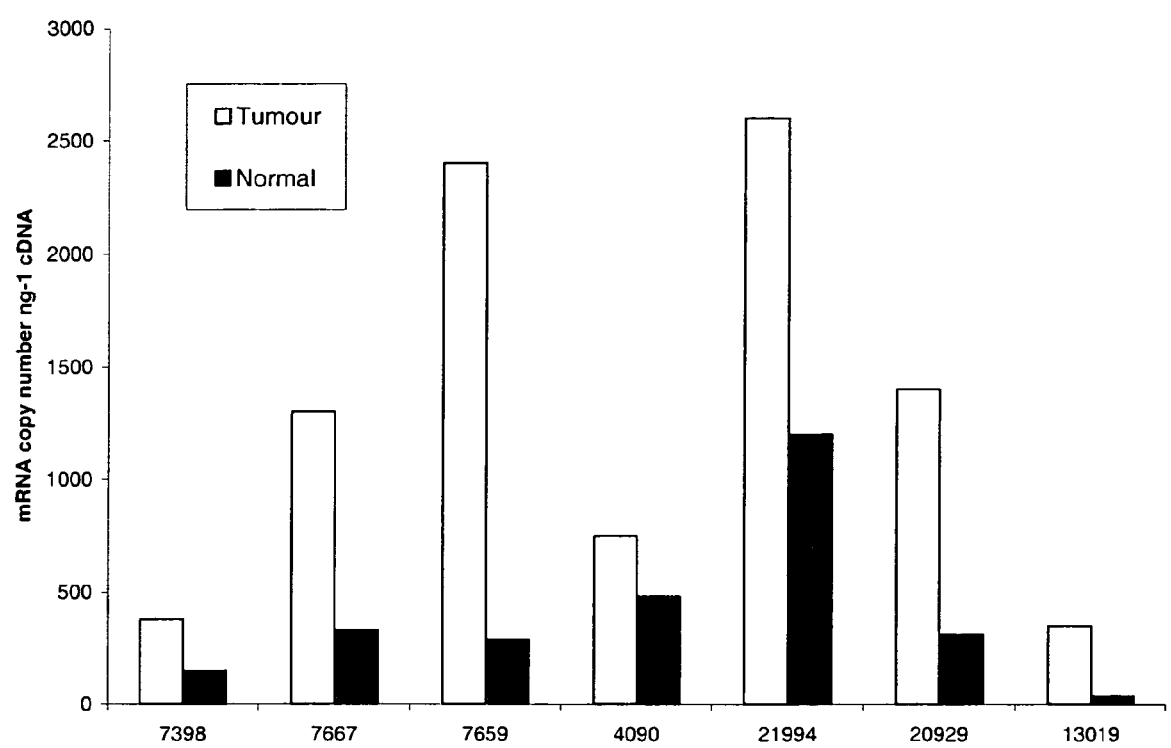

FIG. 3: shows the expression of BCMP 101 mRNA in normal and tumour breast tissues. Levels of BCMP 101 mRNA in matched normal and tumour tissues from seven breast cancer patients were measured by real time RT-PCR. mRNA levels are expressed as the number of copies ng$^{-1}$ cDNA.

Figure 4:
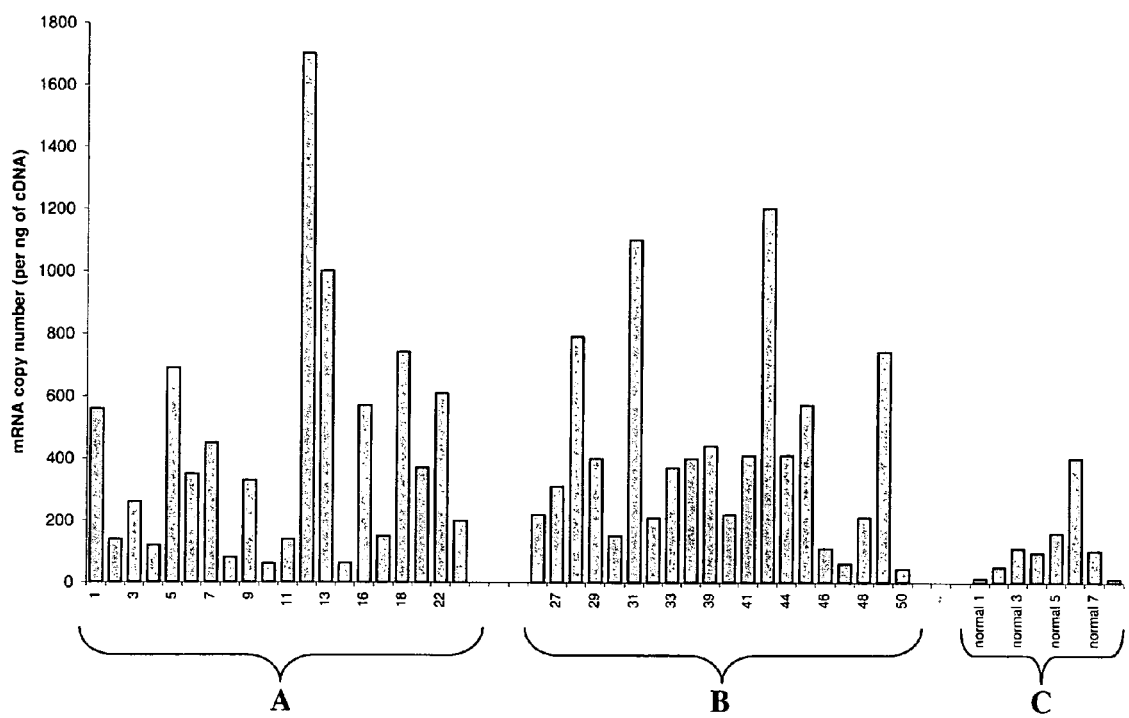

FIG. 4: compares expression of BCMP 101 mRNA in metastatic/non-metastatic breast tumour tissues. A=Samples 1-23, which are derived from tumour samples not involving metastasis to the lymph nodes. B=Samples 26-50, which are derived from tumour samples involving metastases to variable numbers of lymph nodes. C=8 samples from normal breast tissues (reduction mammoplasties). mRNA levels are expressed as the number of copies ng$^{-1}$ cDNA. There is a statistically significant difference between all tumour samples and normal samples (T-test, $p<0.05$).

Figure 5:
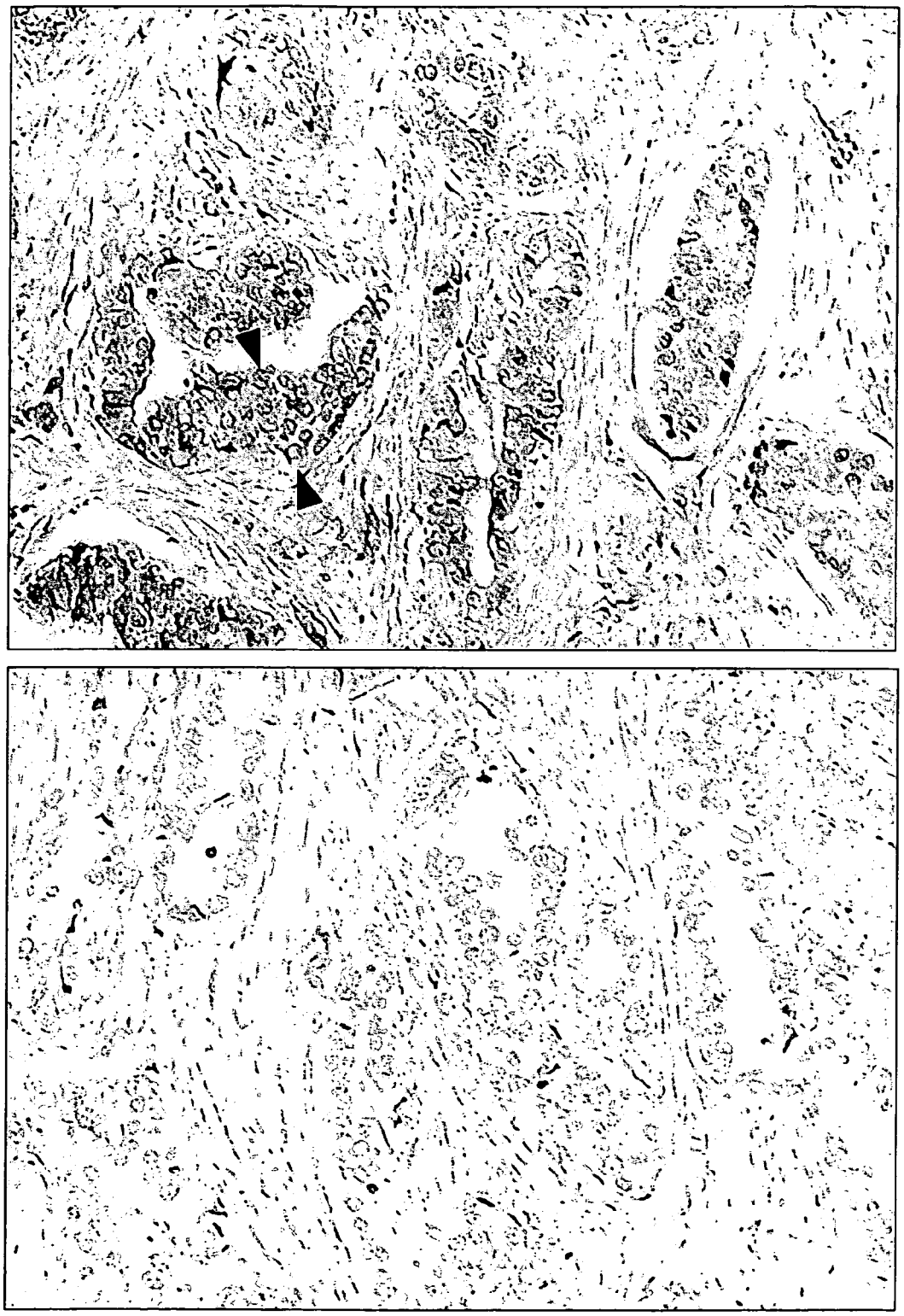

FIG. 5: in situ RT PCR analysis of BCMP 101 expression in sections of invasive ductal breast cancer tissue (upper panel), and consecutive negative control section in which the BCMP 101 primers have been replaced with primers to a control gene (Prostate Specific Antigen) (lower panel). Note the high BCMP 101 expression (dark staining) in a portion of epithelial hyperplasia (typical of breast carcinoma), flanked with two arrowheads in the upper panel.

Figure 6:
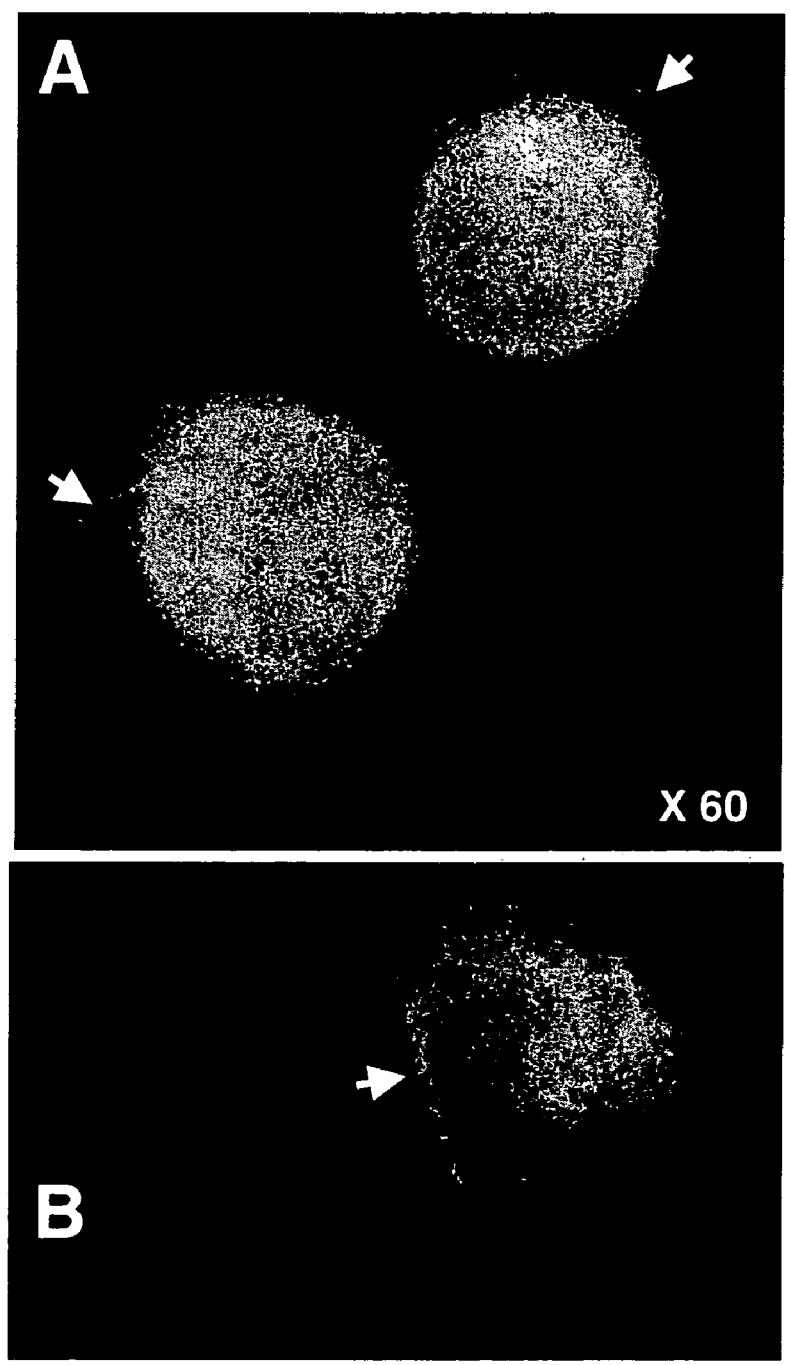

FIG. 6: cellular localisation of BCMP 101 in breast cancer cell lines. Fluorescence microscopy showing expression of C-terminal SuperGlo™ AFP-tagged BCMP101 in MDA-MB468 (A) and T47D (B) cell lines. Membrane localisation is indicated by white arrowheads. Magnification using×60 oil immersion objective.

Figure 7:

FIG. 7: immunohistochemical localisation of BCMP 101 protein expression in breast carcinoma tissue sections. BCMP 101 immunostaining in carcinoma cells is indicated by arrowheads.

EXAMPLE 1

Identification and Cloning of BCMP 101

Protein BCMP 101 was isolated from MDA-MB468 cell membranes. The breast carcinoma cell line MDA-MB-468 (ATCC:HTB-132) was cultured and integral membranes were extracted with the Tx 114 detergent. These were subsequently analysed by two-dimensional gel electrophoresis as described in U.S. Pat. Nos. 6,064,754 and 6,278,794.

Mass Spectrometry

Proteins excised from the 2D gel were digested with trypsin and analysed by MALDI-TOF-MS (Voyager STR, Applied Biosystems) using a 337 nm wavelength laser for desorption and the reflectron mode of analysis. Selected masses for BCMP 101 were further characterised by tandem mass spectrometry using a QTOF-MS equipped with a nanospray ion source, (Micromass UK Ltd.). Prior to MALDI analysis the samples were desalted and concentrated using C18 Zip Tips™ (Millipore). Samples for tandem MS were purified using a nano LC system (LC Packings) incorporating C18 SPE material.

Using the SEQUEST search program (Eng et al., 1994, J. Am. Soc. Mass Spectrom. 5:976-989), uninterpreted tandem mass spectra of tryptic digest peptides were searched against a database of public domain proteins constructed of protein entries in the non-redundant database held by the National Centre for Biotechnology Information (NCBI) and also constructed of Expressed Sequence Tags entries. As a result of database searching, the following amino acid sequence of a tryptic digest peptide of BCMP 101 was determined from a match to a tryptic digest peptide in a conceptual translation of EST AI472043: NSESFAAWCR (SEQ ID NO: 3, shown in FIG. 1).

EST AI472043 corresponds to base pairs 558-1054 of the DNA sequence in FIG. 1. ESTs AI684699 (corresponding to bp 80-565) and AI827549 (corresponding to bp 45-547) were used to establish the full length ORF (note that AI827549 includes the in frame stop codon just upstream of the ATG). The sense primer used to amplify the full length clone was designed to genomic sequences in entry AC021396 (see below Example 3 on chromosomal localisation). The identified protein had a pI of 5.3 and a MW of 39940Da as measured by 2-D gel analysis as described above, the predicted pI and MW for this protein is 5.34 and 34474 respectively.

A Full Length Clone was Amplified by PCR from MDA-MB-468 cDNA:

Preparation of Total RNA and cDNA Synthesis

Total RNA was prepared from cultured cells and tissue samples using Trizol reagent (Life Technologies), according to the manufacturer's instructions, and resuspended in RNAse-free water at a concentration of 1 µg/µl. 1 to 5 µg total RNA were used as a template for cDNA synthesis using an oligo dT primer and the Superscript II reverse transcription kit (Life Technologies). cDNAs were column purified (Qiagen) and eluted at a concentration of 10 ng/µl.

Cloning of BCMP 101 cDNA

The predicted full length BCMP 101 ORF was amplified by PCR from MDA-MB468 cDNAs, using the following primers:

```
                            (SEQ ID NO: 4)
Sense,      5' TGTGCAAATGACCCTGGAGTTG 3';

(SEQ ID NO: 5)
Antisense,  5' GGCTGCTACTGCAAACAGTTCC 3'.
```

Reactions contained 10 ng cDNA and reagents for PCR (Clontech, Advantage-GC 2 PCR kit), and used the following cycling parameters: 1 cycle of 94° C. for 3 minutes, followed by 40 cycles of 94° C. for 30s seconds, 65° C. for 30 seconds, 72° C. for 90 seconds. The PCR products were column purified (Qiagen), cloned into a T/A vector (Invitrogen) and the nucleotide sequence subsequently verified (University of Oxford, Sequencing Facility, UK).

The BCMP 101 sequence (FIG. 1, SEQ ID NO: 1) matches the following GenBank entry CAD10629-NSE2 protein [Homo sapiens]—A novel NS-containing protein (released 24Oct. 2001)).

EXAMPLE 2

Expression of BCMP 101 mRNA in Human Tissues

Real time quantitative RT-PCR was used (Heid, C. A., Stevens, J., Livak, K. J. & Williams, P. M. Real time quantitative PCR. *Genome Res.* 6, 986-994 (1996); Morrison, T. B., Weis, J. J. & Wittwer, C. T. Quantification of low-copy transcripts by continuous SYBR Green I monitoring during amplification. *Biotechniques* 24, 954-958 (1998)) to analyse the distribution of BCMP 101 mRNA in normal human tissues and kidney cancer cell lines (FIG. 2). Note the 40-fold difference between the right-hand scale, used for kidney cancer cell lines, and the left-hand scale, used for normal human tissues, which includes normal kidney.

Quantification of BCMP 101 mRNA by RT-PCR

Real time RT-PCR was used to quantitatively measure BCMP 101 expression in normal human tissue mRNAs (Clontech), kidney cancer cell line mRNAs (Ambion), breast cancer tissues removed during surgery, and normal breast tissue removed during breast reduction mammoplasty. Ethical approval for the normal and tumour breast samples was obtained at surgery (University of Oxford, UK). The primers used for PCR were as follows:

```
                            (SEQ ID NO: 6)
sense,      5' GGTCAACGATCTGTACCGCTAC 3', (SEQ ID NO: 7)
antisense,  5' GCCGATCTTGAACTCGCGCTTG 3'.
```

Reactions containing 10 ng cDNA, prepared as described above, SYBR green sequence detection reagents (PE Biosystems) and sense and antisense primers were assayed on an ABI7700 sequence detection system (PE Biosystems). The PCR conditions were 1 cycle at 50° C. for 2 min, 1 cycle at 95° C. for 10 min, and 40 cycles of 95° C. for 15s, 65° C. for 1 min. The accumulation of PCR product was measured in real time as the increase in SYBR green fluorescence, and the data were analysed using the Sequence Detector program v1.6.3 (PE Biosystems). Standard curves relating initial template copy number to fluorescence and amplification cycle were generated using the amplified PCR product as a template, and were used to calculate BCMP 101 copy number in each sample.

Overall, the distribution of BCMP 101 mRNA was low in normal tissues, with the highest levels of expression in mammary gland, kidney and bladder (130-240 copies $ng^{-1}$ cDNA) (FIG. 2). In contrast, BCMP 101 mRNA was detected at a high level in two kidney cancer cell lines, Human Embryonic Kidney cell line 293 and Wilm's tumour G401 cell line (3300 and 11,000 copies $ng^{-1}$ cDNA respectively) (FIG. 2).

Since BCMP 101 was identified in the MDA-MB-468 breast cancer-derived cell line we measured the distribution of BCMP 101 mRNA in patient matched adjacent normal and tumour breast tissue samples from seven breast cancer patients (FIG. 3). BCMP 101 expression was increased in all tumour samples relative to their matched normal tissues, with four of the samples showing a 4-fold or greater increase in expression. The difference between the paired normal and tumour sample sets was highly statistically significant, with a p-value of 0.014. Thus, BCMP 101 shows a restricted pattern of expression in normal human tissues, and is elevated in some breast tumours, suggesting that this protein has potential as a therapeutic target.

To further examine the expression of this gene in breast cancer tissues, the quantification of BCMP 101 mRNA levels was extended to a further set of 40 tumour samples, 20 from patients with lymph node metastasis and 20 from patients with no lymph node metastasis (FIG. 4). BCMP 101 mRNA expression was elevated in the majority of the carcinoma samples, relative to the normal breast tissue controls, however, there was no significant association of expression with lymph node metastasis.

EXAMPLE 3

Chromosomal Localisation

A Blast search with the BCMP 101 cDNA sequence (FIG. 1) against htgs (High-Throughput Genome Sequences), returns the following GenBank clone: AC021396, mapped to chromosome 8q23.

Furthermore, a gene responsible for Polycystic Kidney Disease (PKD) in a rat model of autosomal dominant PKD has been identified on rat chromosome 5 (Location of the first genetic locus, PKDr1, controlling autosomal dominant polycystic kidney disease in Han:SPRD cy/+rat, Bihoreau Mont., Ceccherini I, Browne J, Kranzlin B, Romeo G, Lathrop G M, James M R, Gretz N., Hum Mol Genet 1997 April;6(4):609-13). A detailed linkage mapping of rat chromosome 5 placed this PKD locus about 25 cM from the proenkephalin gene, which in human is located on 8q23-q24.

A subsequent Blast search of the human genome with the BCMP 101 cDNA sequence maps the gene to GenBank clone AC021396 on chromosome 8, band q24.21.

EXAMPLE 4

In situ RT-PCR

To further illustrate the involvement of BCMP 101 in breast cancer, in situ RT-PCR analysis of BCMP 101 expression has been carried out on sections of invasive ductal breast carcinoma tissues.

Formalin fixed, paraffin embedded breast tissues from patients with ductal carcinoma was sectioned (5 microM thick) onto glass slides (provided by Human Research Tissue Bank, Department of Cellular Pathology, Peterborough District Hospital, Thorpe Road, Peterborough PE3 6DA). Briefly, the tissue was de-waxed in xylene, gradually rehydrated through alcohol and washed in phosphate buffered saline (PBS) before being permeablised in 0.01% Triton X-100 for 3 minutes followed by treatment with Proteinase K for 30 minutes at 37° C.

Direct in situ RT PCR was carried out in a GeneAmp In Situ PCR System 1000 (Perkin Elmer Biosystems) using a GeneAmp Thermostable rTth RT PCR kit (Perkin Elmer Biosystems). The primers used to amplify BCMP 101 were as follows:

```
                                      (SEQ ID NO: 8)
sense,       5'-TTCACCTCTCCGCGGGTAGCCT-3', (SEQ ID NO: 9)
antisense,   5'-GGAAGTTACCCACATATACGGC-3'.
```

The thermal cycling parameters were; 1 cycle of 94° C. for 2.5 minutes followed by 20 cycles of 94° C. for 40 seconds, 60° C. for 50 seconds, and 72° C. for 30 seconds. Amplified product was detectable through the direct incorporation of alkali stable Digoxigenin-11-dUTP (Roche Diagnostics Ltd.) which was added to the reaction mix. After washing in PBS an anti-Digoxigenin-Gold antibody (Roche Diagnostics Ltd.) was incubated on the tissue section for 30 minutes at room temperature, this was followed by a silver enhancement step (Roche Diagnostics Ltd. silver enhancement reagents) during which time the amplified expression product became visible by light microscopy. The tissue was counter-stained with hematoxylin (Dako Ltd.) and images were captured by a digital camera attached to a light microscope (×10 objective).

In the paired images of FIG. 5 the upper panel demonstrates BCMP 101 expression in the breast cancer tissue, the lower panel represents a negative control consecutive section where the BCMP101 primers have been replaced with primers to a control gene (Prostate Specific Antigen). It is clearly apparent from these Figures that BCMP 101 is specifically expressed in the cancerous ductal epithelial cells of this breast cancer tissue (compare with surrounding breast tissue and negative control experiment). For example, a portion of epithelial hyperplasia (typical of breast carcinoma) has been flanked with two arrowheads (upper panel); this shows that the area of dark staining (representing BCMP101 expression) is restricted to the cancer cells.

EXAMPLE 5

Cellular Localisation of BCMP 101 in Breast Cancer Cell Lines

C-terminal tagging with SuperGlo™ green fluorescent protein (GFP) was used to determine the cellular localisation of BCMP 101 in MDA-MB468 and T47D cell lines.

The BCMP 101 full length ORF was PCR cloned into the pQBI25/50-fIN1 vector (Qbiogene) resulting in an in-frame addition of the SuperGlo™(sg)GFP protein to the C-terminus of the expressed protein. Transient transfection of sgGFP-tagged BCMP 101 cDNA into MDA-MB468 and T-47D cell lines was achieved using Superfect™ transfection reagent (Qiagen) according to the manufacturers instructions. Transfected cells were washed in phosphate buffered saline (PBS), fixed in 4% paraformaldehyde for 30 minutes, then washed again in PBS before being mounted in an aqueous-based fluorescent mounting medium (Dako Ltd.). Fluorescence images were captured using a DC300F digital camera attached to a DMIRE2 fluorescence microscope (Leica Microsystems (UK) Ltd.)

Analysis of the cellular location of GFP-tagged BCMP 101 demonstrated high expression in the Golgi and endoplasmic reticulum as well as significant expression associated with the plasma membrane in both MDA-MB468 and T47D cell lines (FIG. 6). Particularly high levels of BCMP101 plasma membrane localisation was observed in areas of cell-cell contact (FIG. 6B)). These data suggest a role for BCMP 101 in the transduction of a cellular signal mediated by cell-cell contact.

EXAMPLE 6

BCMP 101 Expression in Breast Cancer Tissues by Immunohistochemistry

Immunohistochemical analysis was carried out on frozen sections of a breast tumour (from Peterborough Tissue Bank, ref. No 6574-Human Research Tissue Bank, Department of Cellular Pathology, Peterborough District Hospital, Thorpe Road, Peterborough PE3 6DA).

Frozen sections were thawed at room temperature for 30 min, and fixed in acetone at 4 degrees C. for 10 min. The sections were subsequently washed twice in PBS.

Endogenous hydrogen peroxidase activity was quenched by treating the slides in 3% hydrogen peroxidase/PBS for 10 mins, followed by 2 washes in PBS. The tissue was blocked in 10% donkey serum/PBS for 1 hour before addition of 2 microg/ml primary polyclonal antibody (in 2.5% donkey serum).

The BCMP 101 polyclonal antibody was raised in rabbits immunised with a specific peptide (Abcam Ltd., Cambridge, UK). The peptide sequence was chosen for synthesis based on plots of hydrophobicity, antigenicity, surface probability. The peptide was synthesised using Fmoc chemistry with a cysteine residue added to the end to enable specific thiol reactive coupling of Keyhole Limpet Haemocyanin prior to immunisation. The BCMP 101 peptide used was: SYKEVPTADPTGVDR (SEQ ID NO: 10, this sequence is shaded in FIG. 1).

Western blot analysis of T47D and MDA-MB468 cell lysates was used to confirm that the antibody cross-reacted with a single band of the predicted size. Following 3 washes in PBS the tissue sections were incubated with biotin conjugated secondary antibodies (Biotin-SP-conjugated AffiniPure™ Donkey anti-rabbit, Jackson ImmunoResearch) diluted at 1:200 (2.5 microg/ml in 2.5% donkey serum/PBS) for 1 hour. Slides were washed 3 times in PBS and the tissue incubated with Streptavidin-HRP (Jackson ImmunoResearch) diluted 1:100 (5 microg/ml in 2.5% donkey serum/PBS), followed by three 5 min washes in PBS. Antibody signal was detected using DAB substrate solution (Dako Ltd.) according to the manufacturers instructions.

Immunohistochemical analysis of BCMP 101 expression demonstrated very low levels in multiple normal tissues. In contrast, high levels of BCMP 101 immunoreactivity were detected in the carcinoma cells of the breast cancer tissue (FIG. 7).

EXAMPLE 7

Yeast Two-Hybrid Study of BCMP 101 Interacting Factors

Construction of Prey Plasmids

Random-primed cDNA was prepared, ligated into an appropriate vector using methods known in the art, and transformed into electrocompetent cells as described in WO 00/66722 and WO 02/12290.

cDNA was collected from the cells (above) and transformed into yeast strain YHGX13 (MATalpha Gal4delta Gal80delta ade2-101::KAN R, his3, leu2-3, -112, trpl-901, ura3-52 URA3::UASGAL1-LacZ, Met) as described in the above Patent Applications.

Construction of Bait Plasmids

Bait fragments were cloned into appropriate vectors using methods known in the art. Amplification, PCR and screening the collection with the two-hybrid system in yeast was as described in WO 00/66722. Where the number of His+ cell clones <285 the process stamp overlay protocol below is used on all colonies. If the number of His+ cell clones >285 and <5000: then process via the overlay and then the stamp overlay protocols on all blue colonies (see WO 00/66722 sections 2.B and 2.C).

The Stamp Overlay Assay

His+ colonies were grown overnight at 30° C. in microtiter plates containing DO-Leu-Trp-His+Tetracyclin medium with shaking. The day after the overnight culture, the 96 colonies were stamped on a 15 cm plate of DO-Leu-Trp-His. 4 control yeast colonies were spotted on the same plate. After 2 days of growing at 30° C., an overlay assay was performed on this plate with 80 ml of overlay mixture (see WO 00/66722 section 2.B.). After 2 hours of incubation, the plate was photographed with a CCD camera. The blue intensity was quantified by Genetools™ software (SYNGENE) and normalised to the control spots. Positive clones were identified and plasmids rescued and transformed into electrocompetent cells as described in WO 02/12290 and WO 00/66722.

Protein-Protein Interactions

Identification of prey nucleotide sequences was as described (WO 02/12290 and WO 00/66722) or alternatively, prey nucleotide sequences were compared with one another and those which share identity over a significant region (60nt) were grouped together to form a contiguous sequence (Contig) whose identity was ascertained in the same manner as for individual prey fragments (WO 02/12290 and WO 00/66722). Selected Interacting Domains were determined also as described in the latter applications.

Major BCMP 101 Interacting Factors

BCMP 101 interacts with alpha-1 catenin (Swiss-Prot accession P35221) and membrane components of clathrin coated vesicles AP1M2 (GenBank accession NP_005489) and AP47 (GenBank accession NP_115882).

Alpha-1 catenin associates with the cytoplasmic domains of multiple plasma membrane localised cadherins and as such are thought to play an important role in cell-cell adhesion. Interestingly, alpha-1 catenin is mutated in the invasive human colon cancer cell family HCT-8 and is therefore an invasion suppressor gene in human colon cancer (Vermeulen, S. J., Nollet, F., Teugels, E., Vennekens, K. M., Malfait, F., Philippe, J., Speleman, F., Bracke, M. E., van Roy, F. M. & Mareel, M. M. The alphaE-catenin gene (CTNNA1) acts as an invasion-suppressor gene in human colon cancer cells. *Oncogene* 18, 905-915 (1999)). Additional evidence supports an interaction between BCMP101 and alpha-i catenin in breast cancer cells. Firstly, alpha-1 catenin was identified in a proteomic analysis of the same breast cancer cell line (MDA-MB-468) as the one described above in Example 1. Secondly, association of BCMP 101 with alpha-1 catenin accounts for the plasma membrane localisation of GFP-tagged BCMP 101 seen in breast cancer cell lines (FIG. 6A), and in particular the observation that BCMP 101 was plasma membrane associated at sites of cell-cell contact (FIG. 6B). Thus BCMP 101 is associated with a complex of membrane proteins with a known role in tumour progression.

FIG. 6 also shows some cytosolic and Golgi localisation of GFP tagged BCMP 101. This is consistent with the interaction of BCMP 101 with AP1M2 and AP47 which are part of the AP-1 adaptor complex which is recruited from the cytosol onto the trans-Golgi network membrane, where it co-assembles with clathrin into a coat that drives vesicle budding involved in trafficking proteins to other cell membranes including the plasma membrane.

The invention claimed is:

1. An isolated polypeptide, said polypeptide comprising a material selected from the group consisting of: a) an amino acid sequence set out in SEQ ID NO: 1; and b) a fragment of SEQ ID NO: 1, said fragment consisting of SEQ ID NO: 3 or SEQ ID NO: 10.

2. The isolated polypeptide of claim 1, wherein said isolated polypeptide is operably linked to a second amino acid sequence to generate a fusion polypeptide.

3. A composition comprising at least one polypeptide of claim 1 and at least one of pharmaceutically acceptable excipients, adjuvants, carriers and diluents.

\* \* \* \* \*

SEQUENCE LISTING

```
<160> NUMBER OF SEQ ID NOS: 10

<210> SEQ ID NO 1
<211> LENGTH: 310
<212> TYPE: PRT
<213> ORGANISM: Homo sapiens

<400> SEQUENCE: 1
```

```
Met Gly Asn Gln Val Glu Lys Leu Thr His Leu Ser Tyr Lys Glu Val
1               5                   10                  15

Pro Thr Ala Asp Pro Thr Gly Val Asp Arg Asp Asp Gly Pro Arg Ile
            20                  25                  30

Gly Val Ser Tyr Ile Phe Ser Asn Asp Asp Glu Asp Val Glu Pro Gln
                35                  40                  45

Pro Pro Pro Gln Gly Pro Asp Gly Gly Leu Pro Asp Gly Gly Asp
        50                  55                  60

Gly Pro Pro Pro Gln Pro Gln Pro Tyr Asp Pro Arg Leu His Glu
65                  70                  75                  80

Val Glu Cys Ser Val Phe Tyr Arg Asp Glu Cys Ile Tyr Gln Lys Ser
                85                  90                  95

Phe Ala Pro Gly Ser Ala Ala Leu Ser Thr Tyr Thr Pro Glu Asn Leu
            100                 105                 110

Leu Asn Lys Cys Lys Pro Gly Asp Leu Val Glu Phe Val Ser Gln Ala
            115                 120                 125

Gln Tyr Pro His Trp Ala Val Tyr Val Gly Asn Phe Gln Val Val His
        130                 135                 140

Leu His Arg Leu Glu Val Ile Asn Ser Phe Leu Thr Asp Ala Ser Gln
145                 150                 155                 160

Gly Arg Arg Gly Arg Val Val Asn Asp Leu Tyr Arg Tyr Lys Pro Leu
                165                 170                 175

Ser Ser Ser Ala Val Val Arg Asn Ala Leu Ala His Val Gly Ala Lys
            180                 185                 190

Glu Arg Glu Leu Ser Trp Arg Asn Ser Glu Ser Phe Ala Ala Trp Cys
            195                 200                 205

Arg Tyr Gly Lys Arg Glu Phe Lys Ile Gly Gly Glu Leu Arg Ile Gly
        210                 215                 220

Lys Gln Pro Tyr Arg Leu Gln Ile Gln Leu Ser Ala Gln Arg Ser His
225                 230                 235                 240

Thr Leu Glu Phe Gln Ser Leu Glu Asp Leu Ile Met Glu Lys Arg Arg
                245                 250                 255

Asn Asp Gln Ile Gly Arg Ala Ala Val Leu Gln Glu Leu Ala Thr His
            260                 265                 270

Leu His Pro Ala Glu Pro Glu Gly Asp Ser Asn Val Ala Arg Thr
        275                 280                 285

Thr Pro Pro Gly Arg Pro Pro Ala Pro Ser Ser Glu Glu Glu Asp
    290                 295                 300

Gly Glu Ala Val Ala His
305                 310

<210> SEQ ID NO 2
<211> LENGTH: 1054
<212> TYPE: DNA
<213> ORGANISM: Homo sapiens

<400> SEQUENCE: 2
tgtgcaaatg accctggagt tggtttcgct ttctcccctt gcggcggtgt gaacgtgtgt     60
ccgcagcgtg atgggcaacc aggtggagaa attgacccac ctaagttaca aggaagttcc    120
cacggccgac ccgactggcg tggaccggga cgacgggccc cgcattgggg tctcctacat    180
tttctccaat gacgatgagg acgtggagcc gcagccgccg cctcagggge cagatggcgg    240 cggcttgccc gacggtgggg acgggccgcc gccgccccag ccgcagccct acgatccgcg    300
```

```
gctgcacgag gtggaatgct ccgtgttcta ccgggacgaa tgcatctacc agaagagctt    360
cgcgccgggc tcggcggcgc tgagtaccta cacgcccgag aacctgctca acaagtgcaa    420
gccgggcgat ctggtggagt tcgtgtcgca ggctcagtac ccgcactggg ccgtatatgt    480
gggtaacttc caggtggtgc acctgcaccg gctggaggtg attaacagct tcctgactga    540
cgccagccag ggccgtcgcg gccgcgtggt caacgatctg taccgctaca gccgctaag     600
ctccagcgcc gtggtgcgca acgcgctggc gcacgtgggt gccaaggagc gcgagctgag    660
ctggcgcaac tcggagagtt cgccgcctg gtgccgctac ggcaagcgcg agttcaagat     720
cggcggcgag ctgcgcatcg gcaagcagcc ctaccggctg cagattcagc tgtcggcgca    780
gcgcagccac acgctcgagt tccagagtct agaggacctg atcatggaga agcgacgcaa    840
cgaccagatc gggcgcgcgg ccgtgctgca ggagctcgcc acgcacctgc acccggcgga    900
gccggaggag ggcgacagca acgtggcgcg gactacgccg cctcccgggc gccccctgc     960
gcccagctcc gaggaggagg acggagaggc agtggcacac tgatgggcga gctgagcgca   1020
gagctgcgaa ggggaactgt ttgcagtagc agcc                               1054
```

<210> SEQ ID NO 3
<211> LENGTH: 10
<212> TYPE: PRT
<213> ORGANISM: Homo sapiens

<400> SEQUENCE: 3

Asn Ser Glu Ser Phe Ala Ala Trp Cys Arg
1               5                   10

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
tgtgcaaatg accctggagt tg                                              22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggctgctact gcaaacagtt cc                                              22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ggtcaacgat ctgtaccgct ac                                              22

<210> SEQ ID NO 7
<211> LENGTH: 22
<212> TYPE: DNA
<213> ORGANISM: Artificial Sequence
<220> FEATURE:

-continued

```
<223> OTHER INFORMATION: Primer

<400> SEQUENCE: 7
gccgatcttg aactcgcgct tg                                              22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ttcacctctc cgcgggtagc ct                                              22

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ggaagttacc cacatatacg gc                                              22

<210> SEQ ID NO 10
<211> LENGTH: 15
<212> TYPE: PRT
<213> ORGANISM: Homo sapiens

<400> SEQUENCE: 10

Ser Tyr Lys Glu Val Pro Thr Ala Asp Pro Thr Gly Val Asp Arg
1               5                   10                  15
```